(12) United States Patent
Overfield et al.

(10) Patent No.: US 11,793,952 B2
(45) Date of Patent: *Oct. 24, 2023

(54) INTERACTIVE APPARATUS AND METHOD FOR REAL-TIME PROFILING OF INHALATION EFFORTS

(71) Applicant: MANNKIND CORPORATION, Valencia, CA (US)

(72) Inventors: Dennis Overfield, Fairfield, CT (US); Carl R. Sahi, Coventry, CT (US); Benoit Adamo, Mount Kisco, NY (US); P. Kinsey, Sandy Hook, CT (US); Scott McLean, Waterbury, CT (US); John M. Polidoro, Tolland, CT (US); Chad C. Smutney, Watertown, CT (US)

(73) Assignee: MANNKIND CORPORATION, Valencia, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 16/854,669

(22) Filed: Apr. 21, 2020

(65) Prior Publication Data

US 2020/0246561 A1 Aug. 6, 2020

Related U.S. Application Data

(63) Continuation of application No. 15/152,965, filed on May 12, 2016, now Pat. No. 10,675,421, which is a
(Continued)

(51) Int. Cl.
*A61M 15/00* (2006.01)
*A61B 5/087* (2006.01)
(Continued)

(52) U.S. Cl.
CPC ......... *A61M 15/0065* (2013.01); *A61B 5/087* (2013.01); *A61M 15/0021* (2014.02);
(Continued)

(58) Field of Classification Search
CPC ............................................ A61B 5/087–0878
See application file for complete search history.

(56) References Cited

U.S. PATENT DOCUMENTS

| | | | | |
|---|---|---|---|---|
| 4,984,158 A | * | 1/1991 | Hillsman | A61M 15/009 600/536 |
| 5,331,953 A | * | 7/1994 | Andersson | A61M 15/00 128/200.14 |

(Continued)

FOREIGN PATENT DOCUMENTS

| | | |
|---|---|---|
| DE | 102008051515 A1 | 4/2010 |
| WO | 2015003856 A1 | 1/2015 |

(Continued)

OTHER PUBLICATIONS

International Search Report dated Sep. 17, 2019 for International Application No. PCT/US2019/028986 filed on Apr. 24, 2019.
(Continued)

*Primary Examiner* — Joseph D. Boecker
*Assistant Examiner* — Thomas W Greig

(57) ABSTRACT

Described herein are interactive apparatus and methods for sensing and measuring real-time characteristic patterns of a subject's use of a dry powder inhalation system. The devices can be used in a wired or wireless communication mode to communicate with a display to assess the subject's usage of the inhalation system, to evaluate the performance of the inhalation system and/or to detect the characteristics profile of a dry powder formulation emitted from the inhalation system in use.

20 Claims, 17 Drawing Sheets

Related U.S. Application Data continuation of application No. 12/488,469, filed on Jun. 19, 2009, now Pat. No. 9,364,619.

(60) Provisional application No. 61/159,052, filed on Mar. 10, 2009, provisional application No. 61/074,487, filed on Jun. 20, 2008.

(51) Int. Cl.
*G09B 23/28* (2006.01)
*A61M 16/00* (2006.01)

(52) U.S. Cl.
CPC ......... *A61M 15/0025* (2014.02); *G09B 23/28* (2013.01); *A61M 15/008* (2014.02); *A61M 2016/003* (2013.01); *A61M 2016/0027* (2013.01); *A61M 2202/064* (2013.01); *A61M 2205/3375* (2013.01); *A61M 2205/3569* (2013.01); *A61M 2205/3592* (2013.01); *A61M 2205/50* (2013.01); *A61M 2205/502* (2013.01); *A61M 2205/52* (2013.01); *A61M 2206/10* (2013.01); *A61M 2209/086* (2013.01); *A61M 2230/40* (2013.01)

(56) References Cited

U.S. PATENT DOCUMENTS

| | | | | |
|---|---|---|---|---|
| 5,333,106 | A * | 7/1994 | Lanpher | G09B 23/30 128/200.23 |
| 5,469,750 | A | 11/1995 | Lloyd et al. | |
| 5,794,612 | A * | 8/1998 | Wachter | A61M 15/002 128/200.23 |
| 6,328,033 | B1 | 12/2001 | Avrahami | |
| 6,651,651 | B1 * | 11/2003 | Bonney | A61M 15/008 128/200.23 |
| 6,752,145 | B1 * | 6/2004 | Bonney | A61M 15/009 128/200.23 |
| 10,675,421 | B2 * | 6/2020 | Overfield | G09B 23/28 |
| 2002/0090601 | A1 * | 7/2002 | Strupat | A61M 15/0005 434/363 |
| 2003/0235538 | A1 * | 12/2003 | Zierenberg | A61M 15/0021 128/200.23 |
| 2006/0040953 | A1 * | 2/2006 | Leone-Bay | C07D 241/08 544/385 |
| 2006/0130838 | A1 | 6/2006 | Lee et al. | |
| 2007/0023034 | A1 * | 2/2007 | Jongejan | A61M 15/009 128/200.14 |
| 2007/0240712 | A1 | 10/2007 | Fleming et al. | |
| 2009/0151718 | A1 * | 6/2009 | Hunter | A61M 16/209 600/538 |
| 2009/0294521 | A1 | 12/2009 | de la Huerga | |
| 2013/0221097 | A1 | 8/2013 | Day et al. | |
| 2013/0269694 | A1 | 10/2013 | Patton et al. | |
| 2016/0166766 | A1 | 6/2016 | Schuster et al. | |

FOREIGN PATENT DOCUMENTS

| | | |
|---|---|---|
| WO | 2015144442 A1 | 10/2015 |
| WO | 2017178865 A1 | 10/2017 |
| WO | 2017201463 A1 | 11/2017 |

OTHER PUBLICATIONS

European Search Report dated Aug. 3, 2020 for EP Application No. 13161157.6 filed on Jun. 19, 2009.

European Search Report dated Jan. 21, 2020 for EP Application No. 17800280.4 filed on May 19, 2017.

European Office Action issued in connection with corresponding EP Application No. 13161157.6 dated Mar. 3, 2020.

* cited by examiner

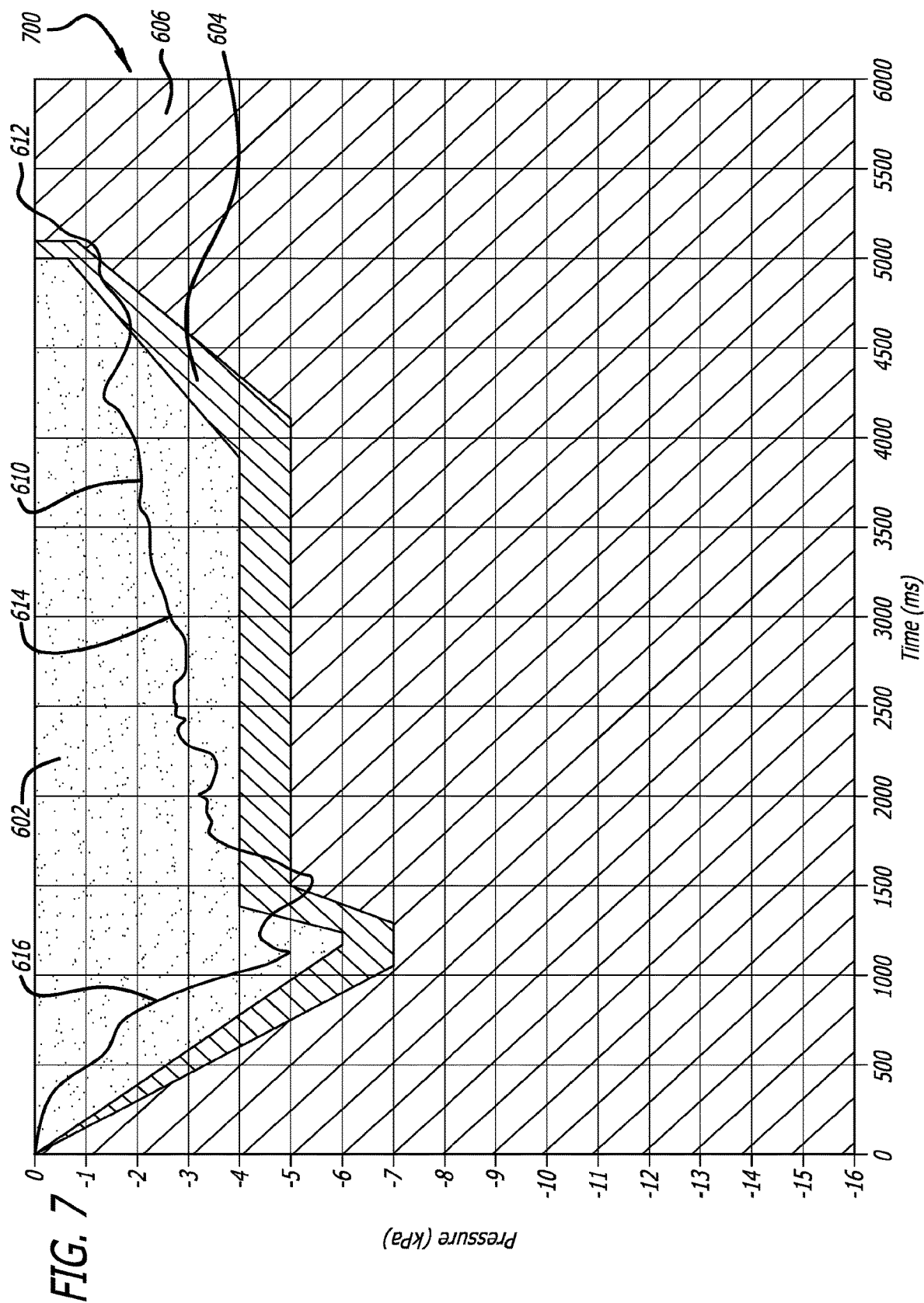

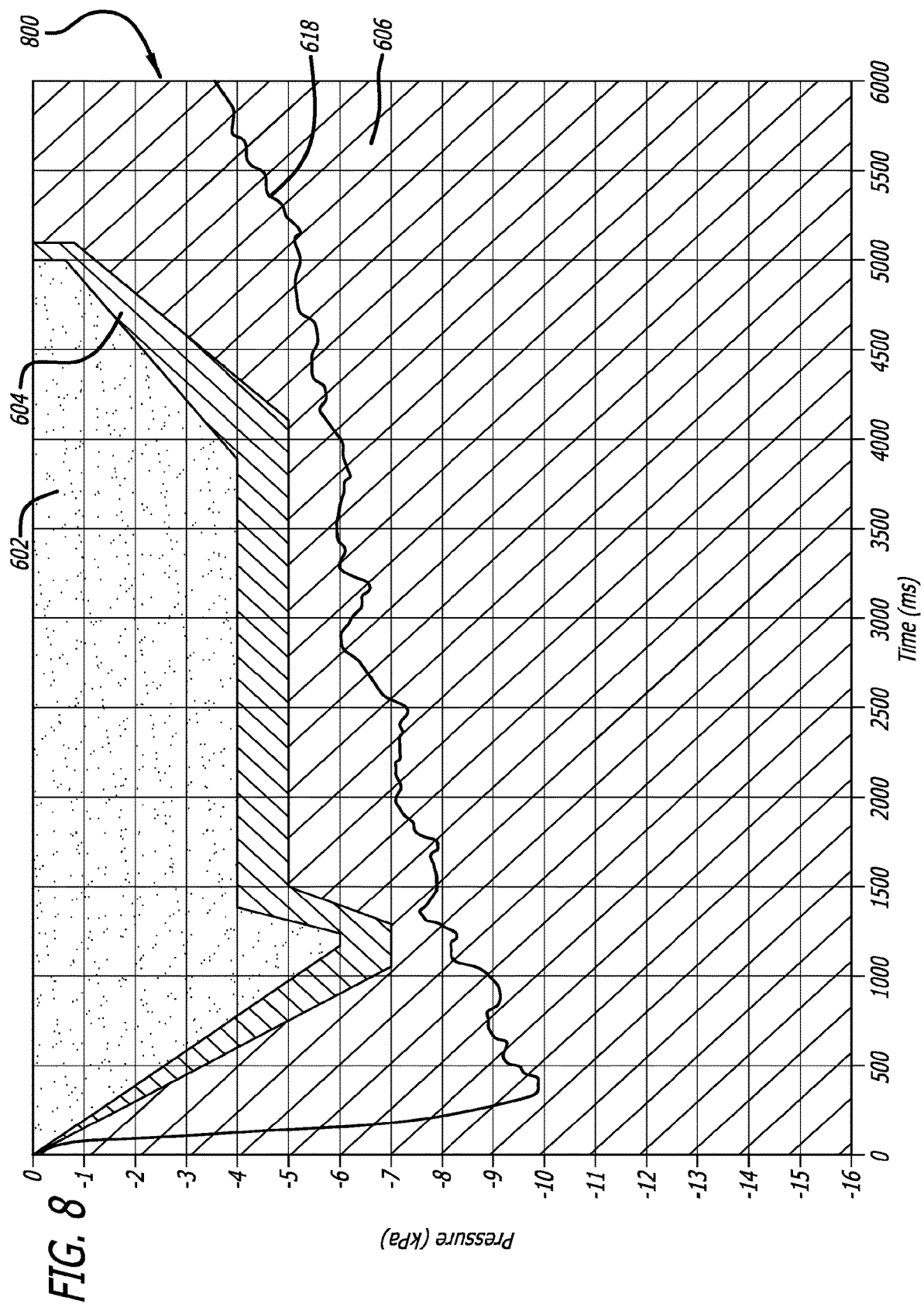

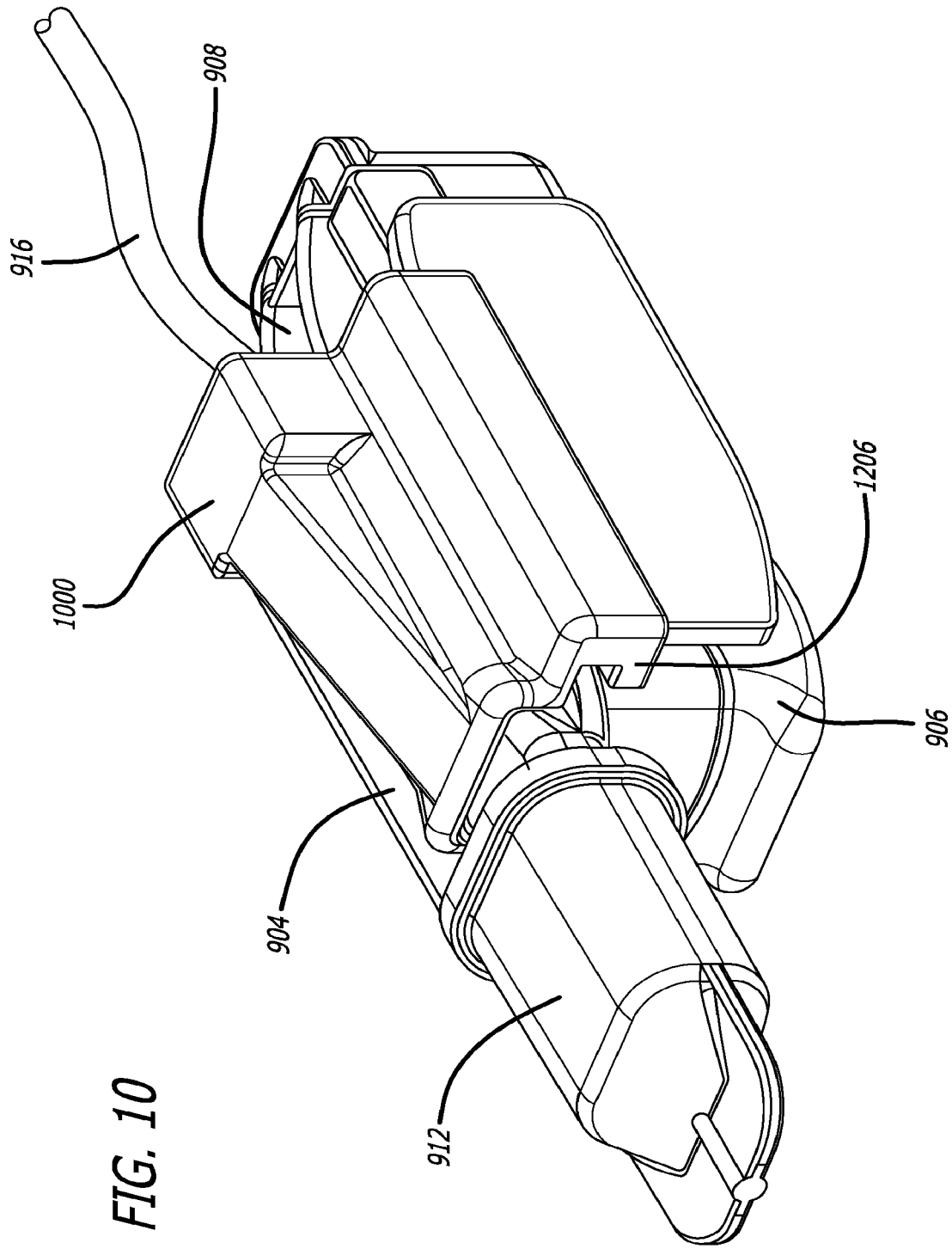

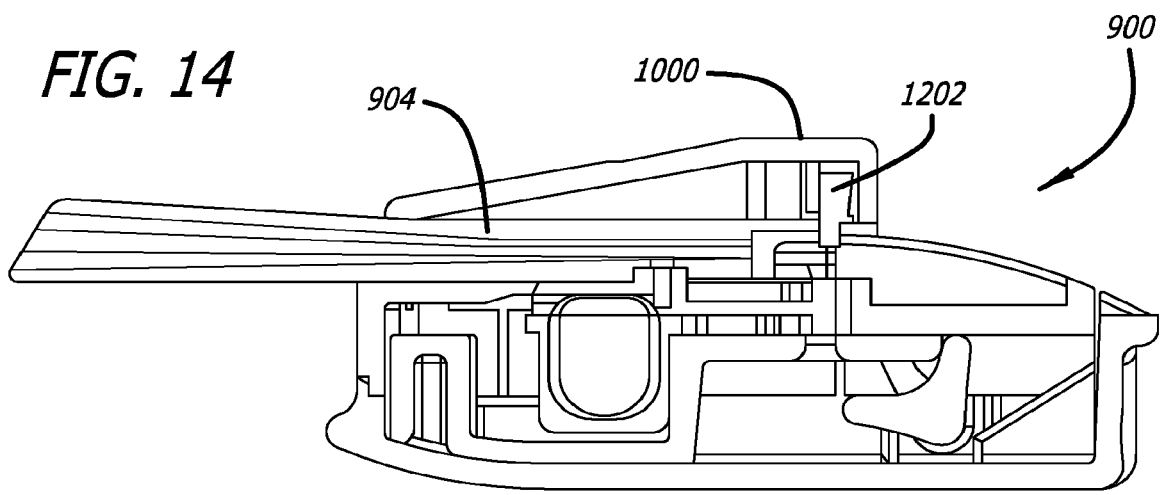
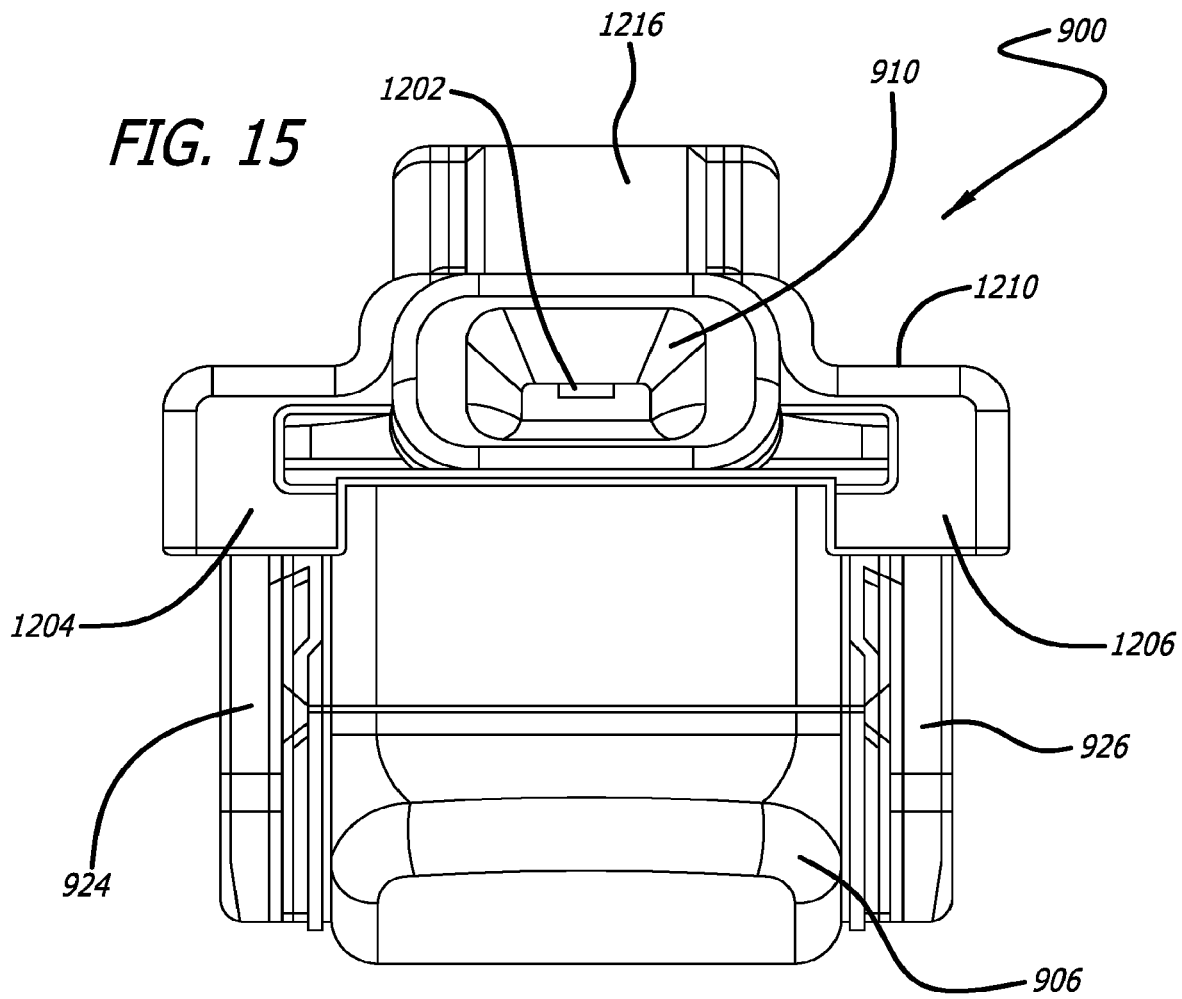

INTERACTIVE APPARATUS AND METHOD FOR REAL-TIME PROFILING OF INHALATION EFFORTS

CROSS REFERENCE TO RELATED APPLICATIONS

This application is a continuation of U.S. patent application Ser. No. 15/152,965, filed May 12, 2016, which is a continuation of U.S. patent application Ser. No. 12/488,469 (now U.S. Pat. No. 9,364,619), filed Jun. 19, 2009, which claims the benefit of U.S. Provisional Patent Application Nos. 61/074,487, filed Jun. 20, 2008, and 61/159,052, filed Mar. 10, 2009, the entire disclosures of which are incorporated herein by reference.

TECHNICAL FIELD

Described herein are interactive apparatus and methods for recording, transferring and displaying key physical measurements based on physiological conditions generated by a subject during an inhalation maneuver in real-time.

BACKGROUND

Inhaler devices for dispensing therapeutic substances via the respiratory tract, in particular, for pulmonary delivery in treating local or systemic diseases are commercially available. For example, nebulizers, devices containing propellants, and dry powder inhalers have been used for the treatment of diseases, such as asthma, respiratory tract infections and systemic disease such as diabetes.

The efficiency of delivering a required dosage of a therapeutic substance to a patient in treating a disease depends on the efficiency of the device, and overall delivery can be enhanced by providing proper feedback mechanisms to a patient during use of the device to teach, for example, proper inhalation techniques to a patient. Improper use of the devices and poor inhalation techniques can lead to lack of efficacy in treating a disease, for example, by administering lower dosages of a therapeutic substance than intended or higher dosages of a therapeutic substance which can be harmful to a patient. To effectively deliver therapeutic substances to the respiratory tract, a patient or user can be trained or coached to use the device in an appropriate manner.

Dry powder inhalers used to deliver medicaments to the lungs contain a dose system of a powder formulation usually either in bulk supply or quantified into individual doses stored in unit dose compartments, like hard gelatin capsules, cartridges, or blister packs. Dosing reproducibility requires that the drug formulation is uniform and that the dose can be delivered to the patient with consistent and reproducible results. Therefore, dosing can be improved by optimizing discharge of a formulation, which is effectuated, for example, by having patients perform proper inhalation maneuvers.

Devices for training patients to properly deliver therapeutic substances by the pulmonary tract are described, for example, in U.S. Pat. No. 5,333,106, which discloses an apparatus for interactive training of a patient in use of an aerosol inhaler, including a feedback display based upon air flow versus volume data using a proper sequence of inhalation steps. U.S. patent application Ser. No. 10/759,859 (Publication No. US 2004/0187869) discloses a training device for medicament inhalers, for example, dry powder inhalers, which is based on measuring pressure differential and displaying a single value corresponding to both inhalation rapidity and inhalation flow rate peak, and includes a dry powder inhaler simulator.

Dry powder inhalers and cartridge systems such as those describe in U.S. Pat. Nos. 7,305,986 and 7,464,706, the disclosures of which are incorporated herein by reference in their entirety for all they teach regarding dry powder inhalers, can generate primary drug particles or suitable inhalation plumes during an inspiratory maneuver by deagglomerating a powder formulation within the inhaler and capsule or cartridge. The benefits of delivering drugs via pulmonary circulation are numerous and, include rapid entry into arterial circulation, avoidance of first pass drug degradation by liver metabolism, ease of use, for example, lack of discomfort compared to other routes of administration such as by injection. These devices have been in use in clinical settings and patients have been properly trained on the use of such inhalers.

There is a need in the art for improvements in design and manufacture of a device for training subjects in proper use of an inhalation system; monitoring patients during use of an inhalation system, and monitoring the performance of an inhalation system, such as presence of leakage or defects. The present disclosure presents apparatus and methods to achieve these goals.

SUMMARY

Described herein apparatus for measuring key inspiratory characteristic parameters during use of an inhalation system. The apparatus and methods for using the apparatus can be useful, for example, in training and/or monitoring a subject requiring the use of an inhaler, for example, a high resistance, dry powder inhaler system for delivery of pharmaceuticals, active ingredients or medicaments to the lungs and pulmonary circulation. Example embodiments of the inhalation systems disclosed herein comprise a display means for visual cues to facilitate training and/or monitoring a subject in achieving an optimal or appropriate inspiratory maneuver for the effective delivery of a therapy via the respiratory system. The systems facilitate the training of subjects for the proper use of an inhalation device in order to achieve a preferred flow profile for that individual so that maximal delivery of a medicament can be attained. The devices and method can also be used to monitor the performance of the inhalation systems, for example, detection of the dose being deliver; quantification of the drug being delivered, duration of discharge of a dose being delivered; number of doses administered to the subject, and to monitor the mechanical integrity of the inhalation system.

In an exemplary embodiment, the apparatus can be made to perform interactively, for example, the apparatus can comprise a wireless communication interface allowing for remote acquisition of data, which can be sent to a computer/microprocessor based-system providing an interactive display of data, storage of data and/or web-based transfer of information. Alternatively, other example embodiments can comprise a wired communication interface.

In one example embodiment, the apparatus or device can be adapted, for example, to a high resistance dry powder inhalation system, such as those described in U.S. Pat. Nos. 7,305,986 and 7,464,706, U.S. patent application Ser. Nos. 12/413,405 and 12/484,125 the disclosures all of which are incorporated herein by reference in their entirety for all they disclose regarding dry powder inhalers. The device can comprise a dry powder inhaler with or without a cartridge containing a pharmaceutical formulation, one or more transducers including, electrical, electronic, electro-mechanical, electromagnetic, photonic or photovoltaic; such as pressure sensors, temperature sensors, sound sensors, and optical sensors; a signal conditioning circuitry and/or software program, a means for electronic signal communication and an output display. In such an example embodiment, the apparatus can be used with an analog or digital sensor, appropriate signal conditioners such as amplification, signal filtering, analog to digital conversion, a microprocessor for onboard processing, a wireless communicator in communication with a remote computer or personal data assistant (PDA) for subsequent signal processing and/or real-time output display. The device can be used to deliver pharmaceutical compositions contained in pre-metered unit dose cartridges containing an active ingredient for delivering to the pulmonary circulation. In alternative example embodiments, the sensing and monitoring device can be adapted onto or within an inhalation system comprising a dry powder inhaler with a cartridge that can be empty, or can contain a dry powder suitable for pulmonary delivery.

Dry powders comprising microparticles suitable for pulmonary delivery are well known in the art including, for example, those disclosed in U.S. Pat. Nos. 6,428,771 and 6,071,497, the disclosures of which are incorporated herein by reference in their entirety for all they disclose regarding microparticles. In respective example embodiments, the dry powders, the active ingredient can be a protein, a peptide, or a polypeptide and combinations thereof, for example, and endocrine hormone such as insulin, glucagon-like peptide-1 (GLP-1), parathyroid hormone or analogs thereof.

In certain embodiments, a dry powder formulation for delivery to the pulmonary circulation comprises an active ingredient or agent, including a peptide, a protein, a hormone, analogs thereof or combinations thereof, wherein the active ingredient is insulin, calcitonin, growth hormone, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, oxyntomodulin, peptide YY, interleukin 2-inducible tyrosine kinase, Bruton's tyrosine kinase (BTK), inositol-requiring kinase 1 (IRE1), or analogs, active fragments, PC-DAG-modified derivatives, or O-glycosylated forms thereof. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin, PTHrP and analogs thereof.

In one example embodiment described herein are dry powder inhalers comprising: a sensor in communication with the dry powder inhaler, wherein the sensor can detect at least one signal type, including pressure, temperature, and sound signals generated from the dry powder inhalation system and can send signal to at least one device for analysis, storage, printing or display. In such an example embodiment, the sensor is configured within the dry powder inhaler or adaptable to the dry powder inhaler and the sensor can be a microphone.

In an example embodiments, the inhalation systems comprises a dry powder inhaler having high resistance to airflow having a resistance value between about 0.065 (kPa)/liter per minute and about 0.200 (kPa)/liter per minute. High resistance inhalation systems can be provided with the sensing and monitoring apparatus. In one embodiment, the sensor can detect intrinsic characteristic signals generated by the inhalation system in use. In another exemplary embodiment, the sensor is a sound sensor which includes a sound detecting device or a microphone, configured to transmit the sound signal by wire or wireless communication mode to at least one another device in the system. The sensing and monitoring apparatus for dry powder inhalers described herein can further be associated with an analog to digital converter which communicates at least one signal such as a sound signal to a microprocessor configured to analyze and process the signal. In another example embodiment, at least one device is an analog to digital converter.

In one example embodiment, monitoring systems are described for a dry powder inhaler comprising: a monitoring device comprising at least one sensor; an analog to digital converter; a data storage medium, wherein the data storage medium includes a set of machine-readable instructions that are executable by a processing device to implement an algorithm, wherein the algorithm comprises instructions for manipulating the data including the steps of: receiving the data from at least one sensor; filtering the data; transforming the data; analyzing the data; and monitoring a patient using the data.

In an example embodiment wherein at least one sensor is a microphone, the monitoring device is provided any place within the inhaler, for example, within the airflow conduits, within the wall of the inhaler, or outside of the inhaler as a separate piece. In another example embodiment, the monitoring device can also be a detachable device that can be mountable on, or attachable to a dry powder inhaler. In yet another example embodiment, the monitoring device provides a graphical display which is a real-time graphical representation of an inhalation.

In another example embodiment, the sound signal is an amplitude of sound signal, a frequency of sound signal or combinations thereof. In yet other example embodiments, the sensor further measures at least one sound signal at different frequencies. In another example embodiment, the dry powder inhalers further comprise a cartridge and the cartridge can comprise a dry powder for pulmonary delivery. Further still, the dry powder can comprise diketopiperazine microparticles and at least one active ingredient. In still another embodiment, at least one medicament comprises insulin, GLP-1, parathyroid hormone, calcitonin, analogues thereof, or combinations thereof.

In a further embodiment, the sensing and/or monitoring device is configured to detect signals from a dose being delivered. In this embodiment, the sensing and monitoring system can detect movement of powder particles within the inhaler and a cartridge system in use from initiation of powder delivery from the cartridge to the end of delivery of the powder particles, wherein the sensor detects variations in the intrinsic characteristics of inhaler sound and powder particle sound emanating from the inhalation system. Data obtained from the detection recordations can be analyzed and correlated to the amount of dose emitted or delivered out of the inhalation system, the time that elapsed for dose delivery, and the performance of the inhalation system.

In another example embodiment, the sensing and monitoring apparatus can be provided as an adaptable, detachable device such as a jacket or saddle structure to a dry powder inhaler. In this embodiment, the removable device facilitates use of the inhalation system, since the structure or configuration of the dry powder inhaler is not modified. Therefore, the same inhaler can be used without the jacket once the characteristic performance of the inhaler has been determined and the subject can properly use it. In embodiments herein, the sensor such as a small microphone, can be advantageously placed in any area of the jacket, including, for example, embedded in the wall of the jacket or adaptor, or extending from the walls of the jacket. In this embodiment, the sensing and monitoring apparatus offers greater resolution of sound characteristics emanating from the dry powder inhaler and cartridge system in use.

In one example embodiment, methods are described for measuring pressure differential during an inhalation maneuver, the methods comprise: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, said at least one frequency of sound signal, or combinations thereof using an algorithm provided with a microprocessor in a computer system to generate a data set; and displaying, printing, or storing the data set as a function of time and pressure.

In further embodiments described herein are monitoring systems for a dry powder inhalers comprising: a monitoring device comprising at least one sensor; an analog to digital converter; a data storage medium, the data storage medium including a set of machine-readable instructions that are executable by a processing device to implement an algorithm, the algorithm comprising instructions for manipulating the data including the steps of: receiving the data from the at least one sensor; filtering the data; transforming the data; analyzing the data; and monitoring a patient using the data.

Even further still, in one embodiment described herein are methods for measuring pressure differential during an inhalation maneuver, comprising: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, the at least one frequency of sound signal, or combinations thereof using an algorithm provided with a computer system to generate a data set; and displaying, printing, or storing the data set as a function of time and pressure.

In other embodiments described herein are interactive dry powder inhalation systems for monitoring an inhalation performed by a user, comprising: a dry powder inhaler comprising a cartridge and having a resistance to flow values between 0.065 (kPa)/liter per minute and 0.200 (kPa)/liter per minute; a transducer configured to detect a signal generated from the inhaler in use, and a display device configured to display in real-time an inhalation maneuver performed by a user. In another embodiment, the transducer senses and measures a pressure differential within the inhaler. Further still, the transducer can be a flow meter configured to sense and measure flow rate through air conduits of the dry powder inhaler. The transducer can be, for example, a microphone configured to sense and measure a sound signal generated from within the inhaler.

In still other embodiments described herein are sensing and monitoring devices for adapting to a dry powder inhaler, comprising: a detachable device structurally configured to adapt to a dry powder inhaler; said detachable device comprising a microphone for detecting sound generated in said dry powder inhaler; and wherein the dry powder inhaler has a resistance to flow value between 0.065 (kPa)/liter per minute and 0.200 (kPa)/liter per minute.

Further, in one embodiment, sensing and monitoring devices are described for a dry powder inhalation system, wherein the dry powder inhalation system comprises a dry powder inhaler and a cartridge and the sensing and monitoring device comprises a microphone configured to detect sound signals generated from a dry powder formulation emitted from the dry powder inhalation system.

BRIEF DESCRIPTION OF THE DRAWINGS

FIG. 7 graphically illustrates an inhalation maneuver performed by a subject only coached to take a deep breath.

FIG. 8 graphically illustrates an inhalation maneuver performed by a subject properly trained to use a dry powder inhaler using the training device.

FIG. 10 illustrates an isometric view of yet an alternate embodiment of a sensing and/or monitoring device provided as part of a jacket adapted to a dry powder inhaler.

FIG. 14 illustrates a side view of a dry powder inhaler in cross-section through its mid-longitudinal line with a cartridge in place and equipped with a sensing and/or monitoring device.

FIG. 15 illustrates a proximal view of a dry powder inhaler equipped with a sensing and/or monitoring device.

DETAILED DESCRIPTION

Disclosed herein are apparatus and/or devices with an interactive system and methods for measuring or monitoring real-time changes in pressure or pressure drop and/or flow from a subject during an inhalation maneuver. The devices can be used for training a subject to maximize efficiency of their respiratory maneuvers in conjunction with an inhalation device, and can also be used for monitoring inspiration during delivery a medicament, to detect proper dose delivery, timing of dose delivery and proper performance of the inhalation system in use. In one example embodiment, the sensing and monitoring apparatus can be applied in conjunction with a high resistance inhaler.

The apparatus comprise a transducer or sensor which can convert at least one measurand, including, pressure, air flow, air volume, humidity, and temperature, to an electrical signal. The device further includes appropriate signal conditioning circuitry, such as signal filtering, amplification and analog to digital conversion, and processing circuitry such as a microprocessor, wired or wireless communication interface and the like to transfer the generated signal in real-time to a receiving computer or personal data assistant (PDA) for display of the signal. In one embodiment, the output display can be and interactive display so that the display device provides a visual aid for teaching a subject to perform repeatable inhalation maneuvers in real-time, thereby facilitating proper inhalation delivery of medicament. In another example embodiment, the data can be stored to be analyzed at a later date.

FIGS. 1 through 4 illustrate an example dry powder inhaler training device. The training devices interactive systems described herein have been adapted to a high resistance dry powder inhaler as disclosed in U.S. Pat. Nos. 7,305,986 and 7,464,706, U.S. patent application Ser. No. 11/934,643 (US 2008/0053437), Ser. No. 11/949,707 (US 2008/0127970), Ser. No. 12/102,625; and other high resistance dry powder inhalers are disclosed in U.S. patent application Ser. Nos. 12/413,405; 12/484,125, the disclosures of which are incorporated herein by reference herein for all they disclose regarding dry powder inhalers.

Figure 1:
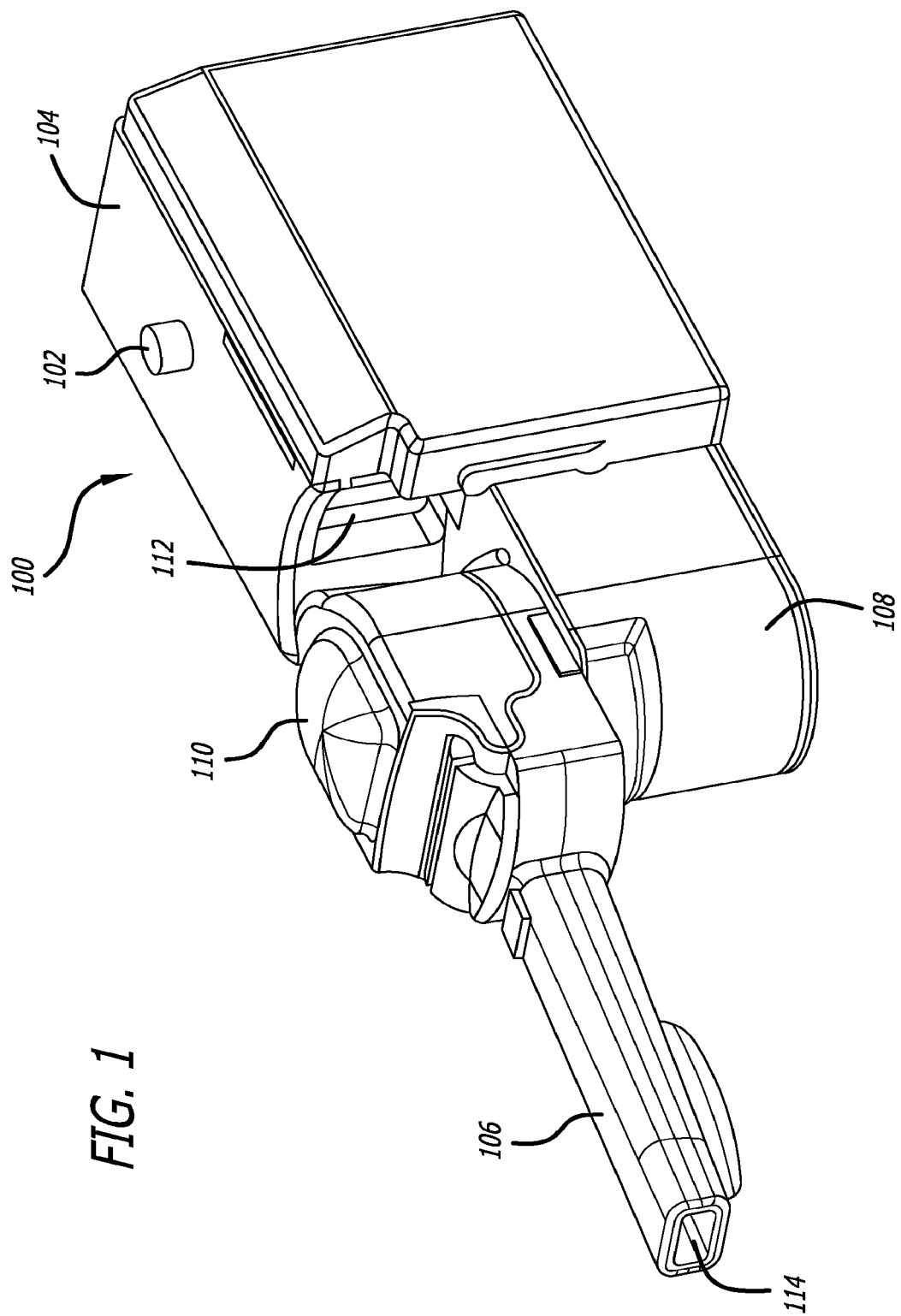
FIG. 1 illustrates an isometric view of the right side of an embodiment of a dry powder inhaler training apparatus.
Figure 2:
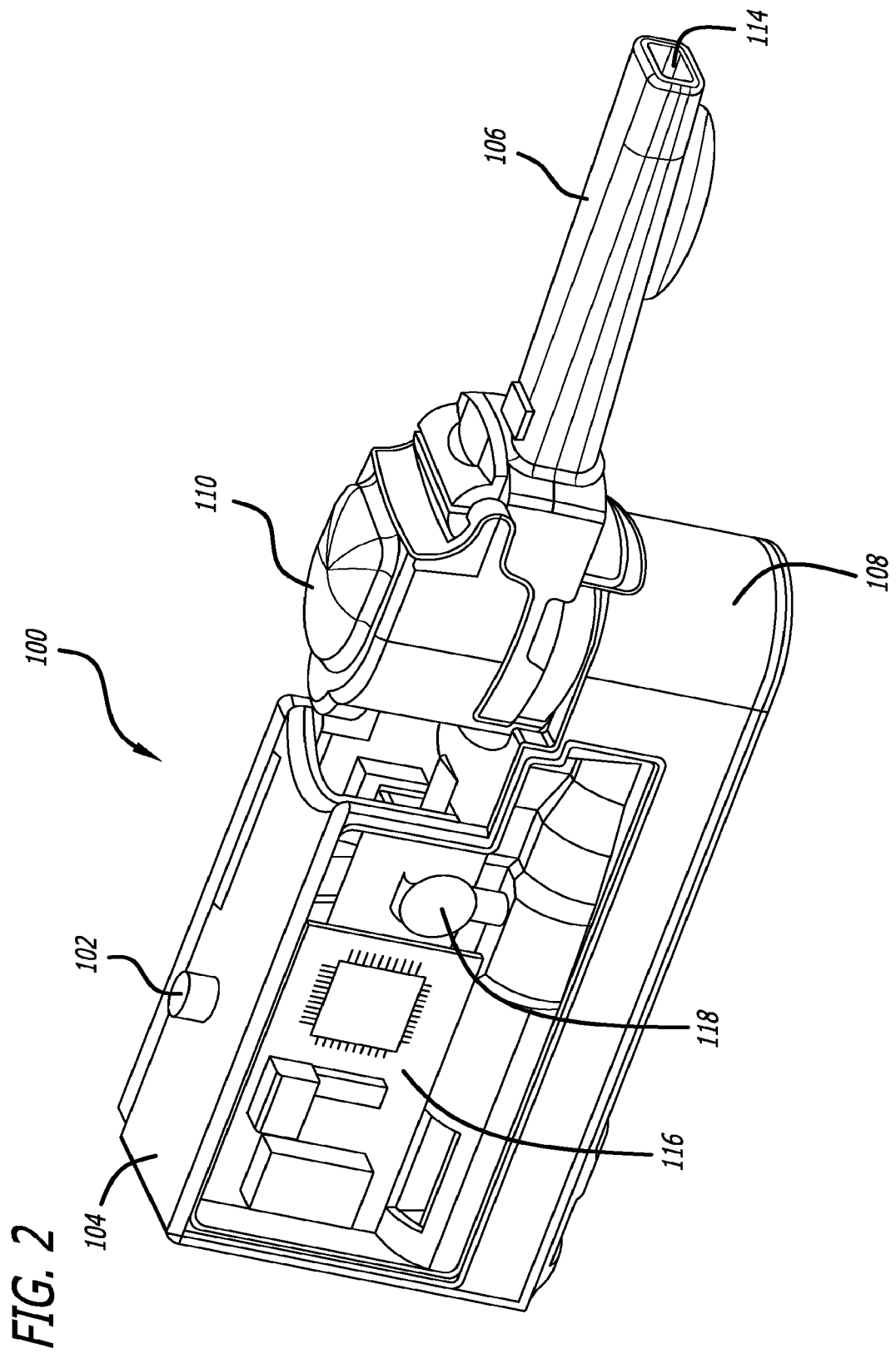
FIG. 2 illustrates an isometric view of the left side of the embodiment of FIG. 1, wherein part of the housing has been removed to show internal component parts of the dry powder inhaler training device.
Figure 3:
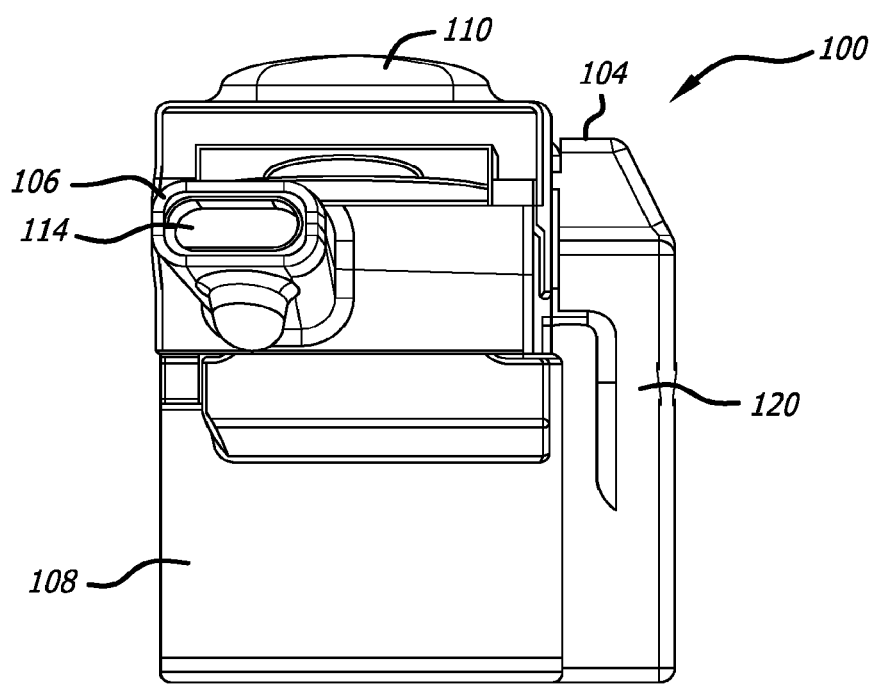
FIG. 3 illustrates a back view of the embodiment of FIG. 1.

Training device 100 comprises activator button 102, housing 104, mouthpiece 106, mixing section 108, a cap or lid 110 over mixing section 108, air inlet port 112 and air outlet port 114. An air conduit is established between air inlet port 112 and air outlet port 114. FIG. 2 illustrates training device 100 with left panel (not shown) of housing 104 removed showing the position of signal processing/interface board 116 and sensor 118 within housing 104. FIG. 3 illustrates a back view of training device 100 showing housing 104 having a compartment with cover 120 on the right side for accommodating a power source.

Figure 4:
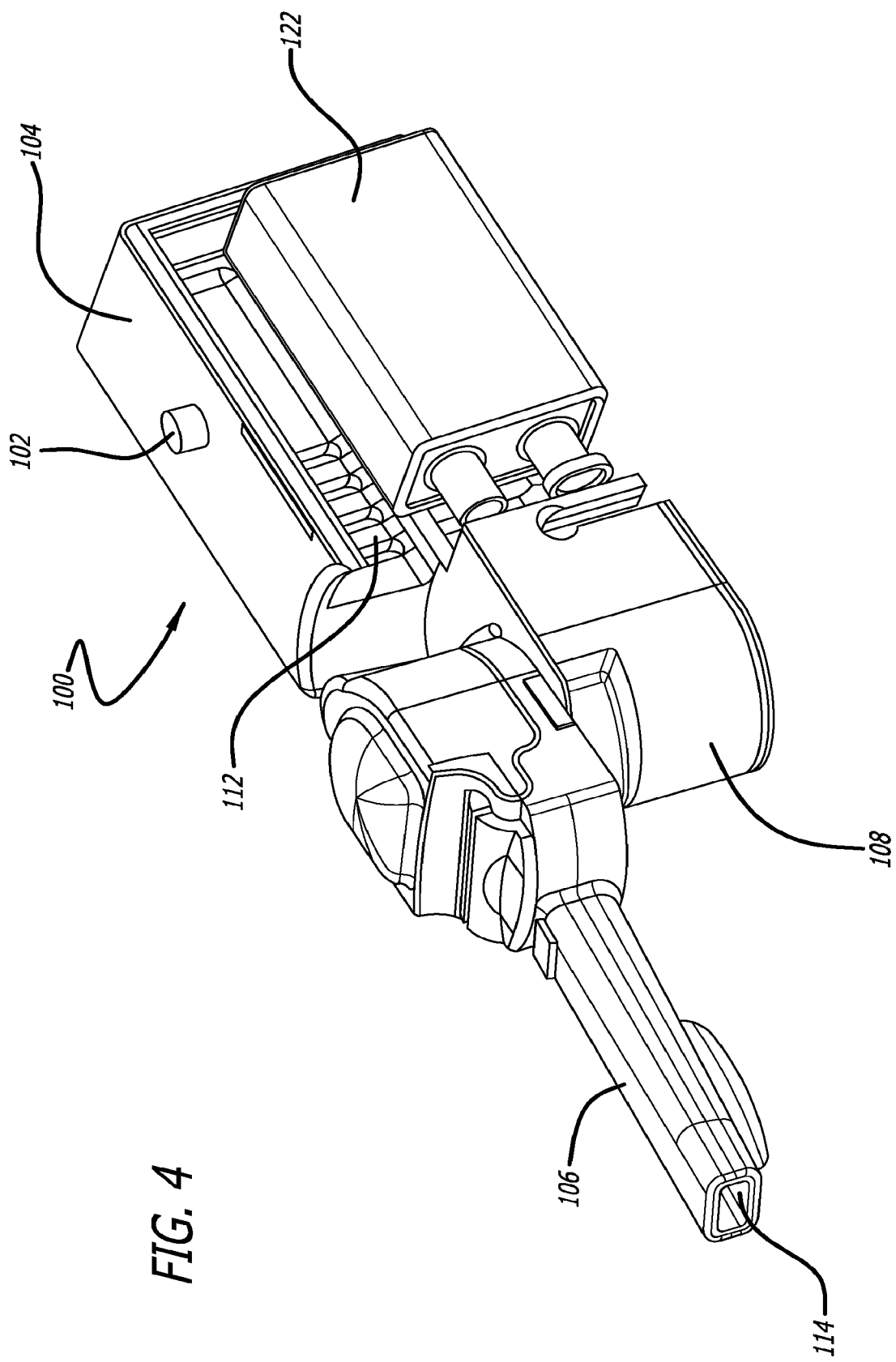
FIG. 4 illustrates an isometric view of the right side of the embodiment of FIG. 1 with the device cover removed to show additional component parts in the interior of the device.

In one example embodiment, sensor 118, in an analogue form, is placed within housing 104 and detects pressure differential from training device 100 when training device 100 is turned on by depressing activator button 102 which is connected to a power source, such battery 122 illustrated in FIG. 4, that also provides power to the system. Sensor 118 can be placed at any point within the air conduit of training device 100. In some example embodiments, sensor 118 can be placed in the air conduit within housing 104. In other example embodiments, sensor 118 can be placed within the mixing chamber (not shown) or the air conduit of mouthpiece 106.

Figure 5:
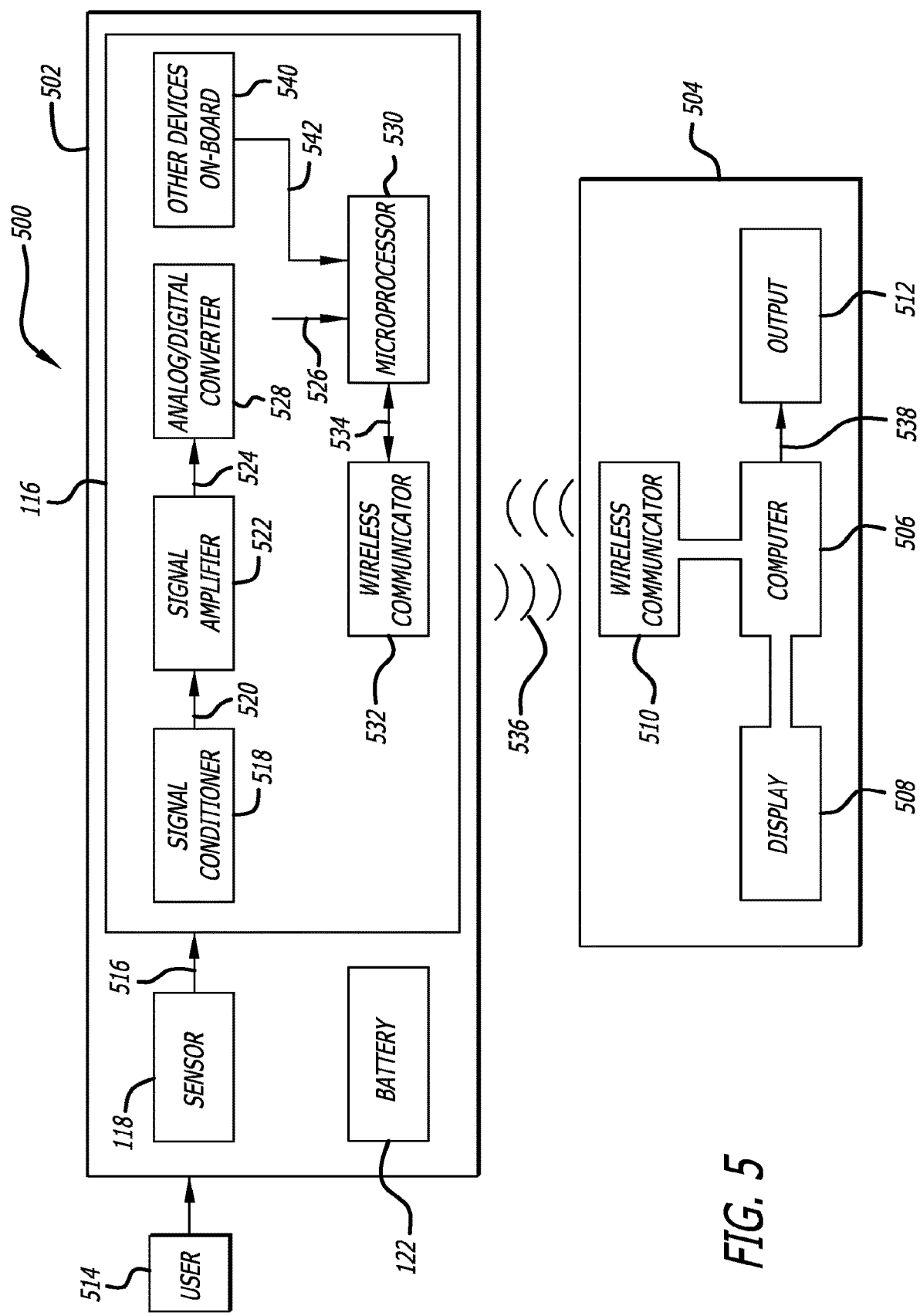
FIG. 5 illustrates a block diagram of the overall training system disclosed herein.

FIG. 5 illustrates a block diagram for an inhaler training device, such as training device 100, showing its various operational component parts. In FIG. 5, system 500 comprises two components, inhaler training device 502 and processing system 504. Processing system 504 can include a PDA or computer 506, display 508, wireless communicator 510 and output 512 which can be in the form of digital storage, a web interface, a print out or the like. In this example embodiment, a user can activate inhaler training device 502 by depressing a power button, for example button 102 on training device 100, with processing system 504 also activated. When the software program integrated with computer 506 is ready, a start signal appears on display 508. With the system activated, inhalation 514 generates a pressure drop in inhaler training device 502 which is transduced to an electrical signal by sensor 118. In this embodiment, the sensor 118 can be a pressure, flow, sound, optical, gas, humidity, or temperature transducer that is either analogue or digital. Electrical signal 516 from sensor 118 is then transmitted to signal conditioner 518 to remove unwanted signals, such as signal noise. Conditioned electrical signal 520 is then transmitted to signal amplifier 522 wherein conditioned electrical signal 518 can be amplified to a predetermined voltage range, and transmitted as amplified signal 524. Amplified signal 524 is then converted to digital signal 526 through analog to digital converter 528. Digital signal 526 then passes through microprocessor 530 and into second wireless communicator 532 through connection 534 for transmission to computer 506, having wireless communicator 510 for receiving wireless signal 536. A software program built into/programmed into microprocessor 530 or computer 506 converts electrical signal 516 to a pressure value which can be displayed graphically. In certain embodiments, a baseline curve for inhaler training device 502 is provided as a reference standard to guide the user's inhalation maneuver. Therefore, during an inhalation, a user can visually compare his/her inhalation maneuver to the baseline standard. In this manner, the user can alter his/her inhalation effort to conform to the requirements of the standard. The displayed data for each inhalation performed by a subject can be saved via second connection 538 to output 512 wherein the data can be stored or transferred accordingly. For example, output 512 can be in the form of a flash drive or printer, or transmitted via email to a physician for review or further training as needed. In one embodiment, signals from the inhalation training device can be transmitted to the computer/PDA and signals from the computer/PDA can be received by the inhalation training device, thereby establishing a two way communication between the two components.

Further, other on-board devices 540 can send and receive data from microprocessor 530 through one or more cable 542. For example, other on-board devices can include digital output sensors, temperature sensors, light emitting diodes (LEDs), sound warning devices, and other on-board sensors.

Other configurations of block diagram 500 can also be configured, for example, following the signal amplification amplified signal 524 can be directly sent to computer 506 via second wireless communicator 532 and the computer can do the analog to digital conversion and other required analysis steps.

Figure 6:
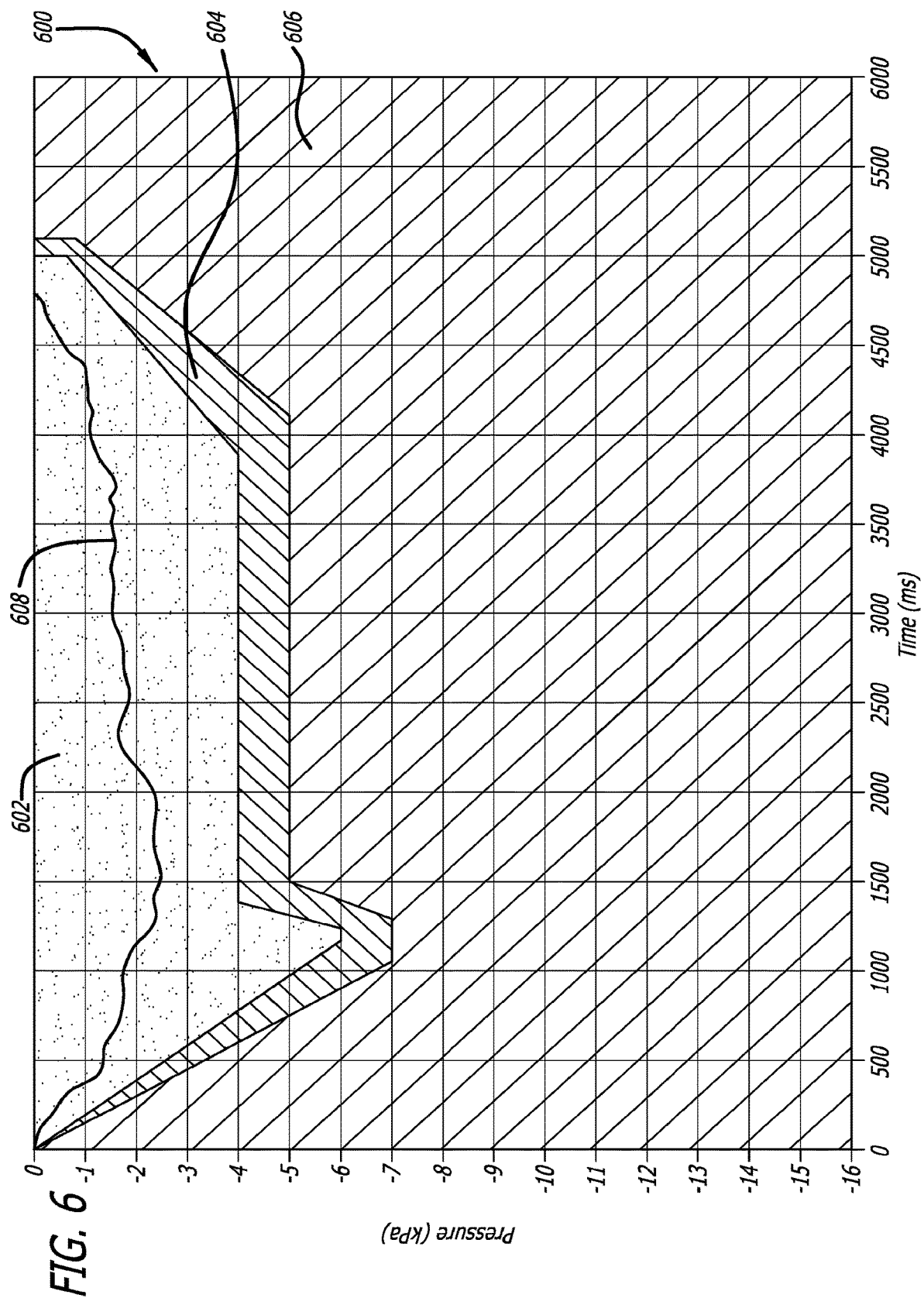
FIG. 6 graphically illustrates an inhalation maneuver performed by a subject without coaching.

Exemplary data from training sessions with a subject are illustrated in FIGS. 6 through 8. Each figure depicts a graph (600, 700, 800) of data displayed by the training systems described herein after an inhalation maneuver. The graphs are plotted as pressure in kPa on the y-axis and time in milliseconds on the x-axis. A baseline inhalation performance standard for training device 100 is shown as region 602 which is bordered by a warning region 604 and an acceptable or preferred region 606. Regions 602, 604 and 606 can be provided in different colors to facilitate discernment of regions in monitoring an individual's performance during an inhalation. Region 602 can be, for example, depicted in red, indicating that the inhalation maneuver did not meet the baseline requirement; therefore, the delivery system would not be optimal to deliver a medicament effectively. Warning region 604 can be depicted in yellow indicating a warning that the inhalation maneuver is nearing the unacceptable performance effort. Preferred region 606 can be depicted in green indicating that the inhalation performance is in the acceptable efforts to effectively deliver a medicament.

FIG. 6 graphically illustrates an example of an inhalation maneuver performed by a subject who has received no training and is not allowed to see the screen display of the computer during the inhalation maneuver. The results of this inhalation are plotted as curve 608. As graphically illustrated in FIG. 6, the inhalation effort by the subject falls in the unacceptable region 602 during the entire inhalation procedure.

FIG. 7 graphically illustrates results of an inhalation maneuver of a subject who has received some guidance on the use of a device and is allowed to look at a computer screen displaying the inhalation effort during the maneuver. In this maneuver and as shown by curve 610, the subject inhaled for an acceptable period of time, as indicated by end point 612 falling within preferred region 606, but did not inhale quickly enough or with enough effort to attain acceptable values, as indicated by regions 614 and 616 which fall within region 602.

FIG. 8 graphically illustrates an example of an inhalation maneuver performed by a subject who has received complete training and is allowed to see the display screen on a computer while performing the inhalation. As can be seen by curve 618, the subject performed entirely within acceptable values in region 606.

The graphs illustrated in FIGS. 6-9 and 19 can be incorporated into a computer program and captured as a screenshot therefrom. Other features of the devices and systems described herein can be controlled using a computer or microprocessor and visualized through an onscreen display.

In some example embodiments disclosed herein, one or more key parameters can define an acceptable inhalation maneuver, including, total inhalation time, peak inspiratory pressure, time to peak inspiratory pressure and average pressure from peak to about 75% of the total inhalation time. In certain embodiments, the total inhalation time can be greater than 5 seconds, the peak inspiratory pressure can be greater than about 6 kPa, time to peak inspiratory pressure can be less than about 1.1 seconds and the average pressure from peak inhalation to 75% of total inhalation time is about 4 kPa. These values are representative of values for training device 100, and can be modified for alternate inhaler training devices, depending on the performance parameters required for optimal delivery of the medicament of the inhaler, including resistance.

Figure 9A:
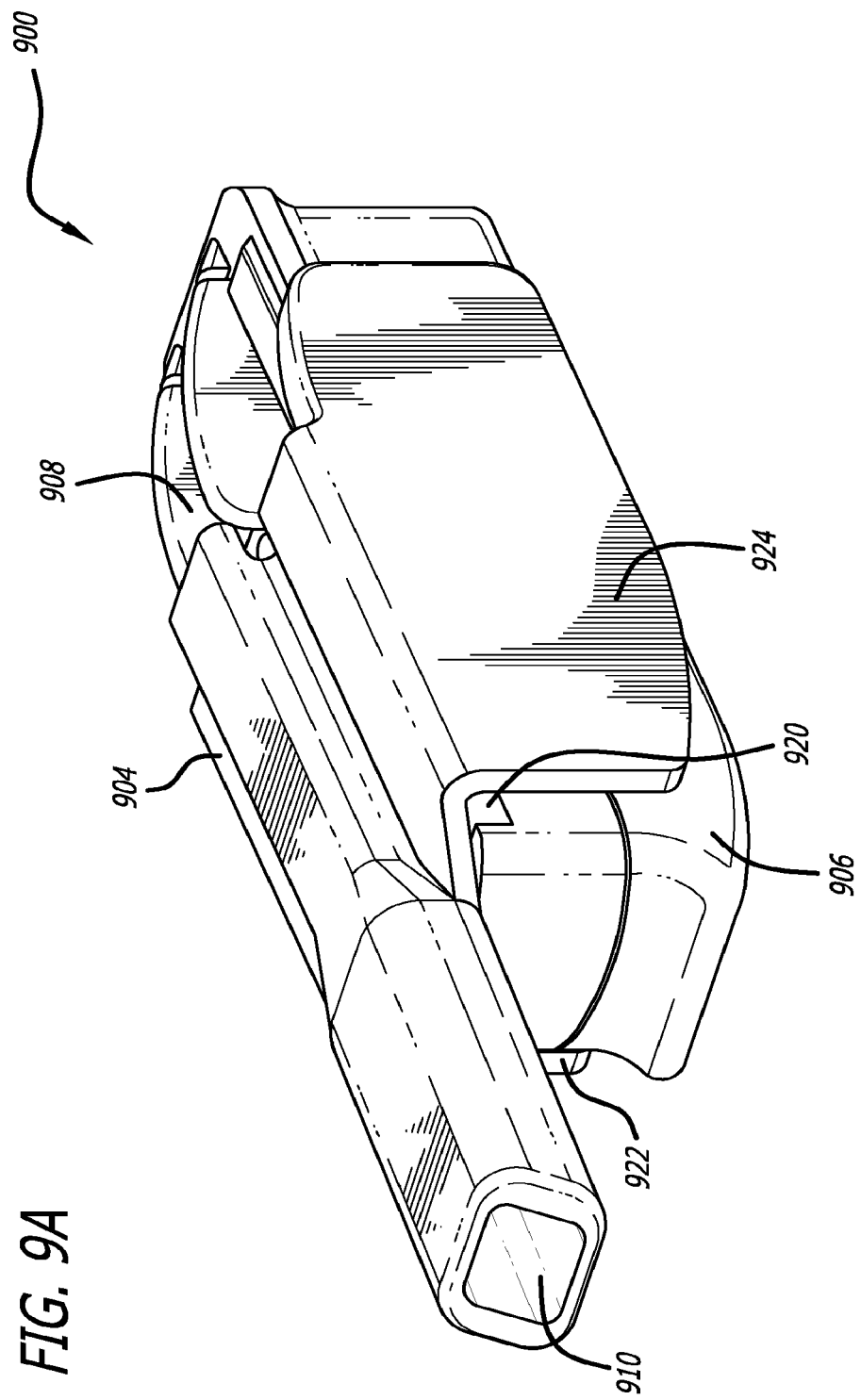
FIGS. 9A and 9B illustrate isometric views of an alternate embodiment of an inhaler with (9B) and without (9A) an integrated sensing and monitoring device.
Figure 9B:
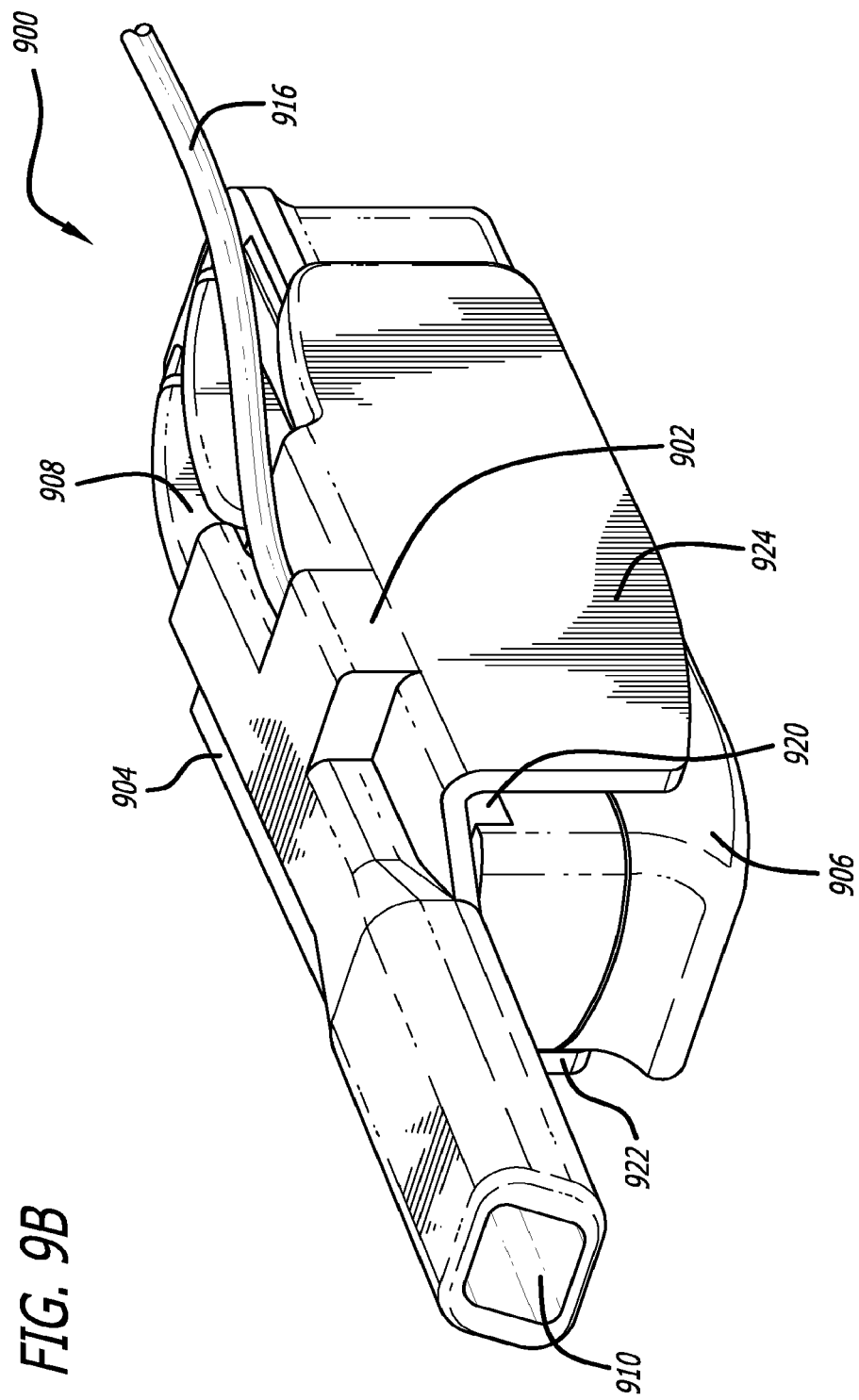

In another example embodiment illustrated in FIGS. 9A and B, dry powder inhaler 900 can be provided with a sensing and/or monitoring device 902 which can monitor and/or sense signals generated by or within dry powder inhaler 900 during an inhalation maneuver by a patient. FIG. 9A illustrates dry powder inhaler 900 without a sensor device either integrated into the device or attached thereto. Alternatively, in an example embodiment depicted in FIG. 9B, monitoring device 902 can be provided as an integral part of dry powder inhaler 900 on mouthpiece 904 or housing 906 as desired. Dry powder inhaler 900, as depicted in FIG. 9B, has monitoring device 902 adapted within the inhaler, which comprises mouthpiece 904 and housing 906. In one embodiment, the sensor can be integrated within the component walls of inhaler 900, including the mouthpiece, housing, sled or to project into one of the flow pathways of the inhaler. Dry powder inhaler 900 comprises an air conduit with an air inlet 908, air outlet 910 and optional mouthpiece cover 912 (FIG. 10). Monitoring device 902 including a small or miniature microphone is provided within dry powder inhaler 900 configured with mouthpiece 904 and is provided with leads 914 (FIG. 13), which can be connected to an analog to digital converter, a display device, and/or a computer.

Figure 11:
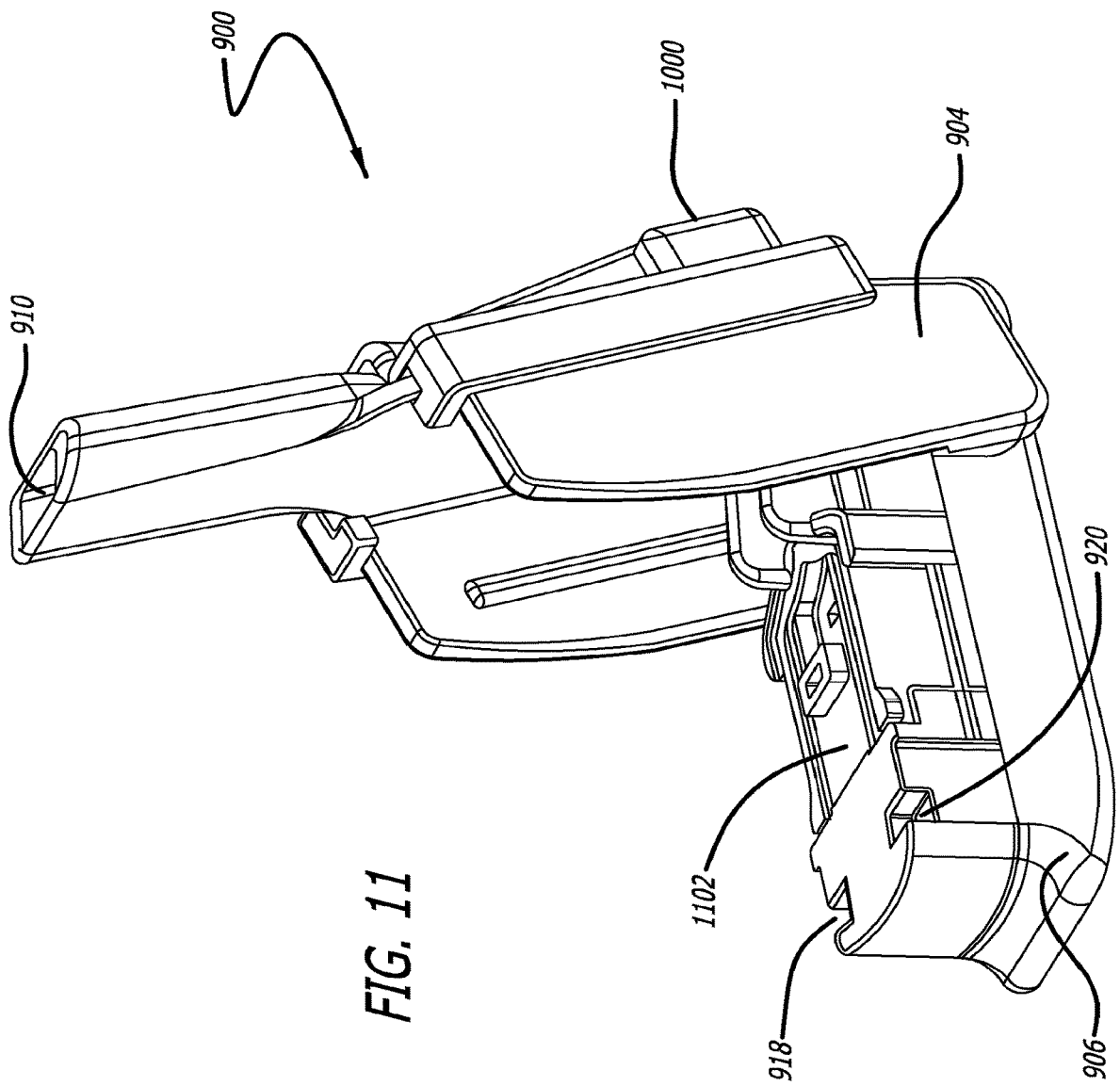
FIG. 11 illustrates an isometric view of the sensing and/or monitoring device illustrated in FIG. 10, wherein a dry powder inhaler system is depicted in an open configuration.
Figure 12:
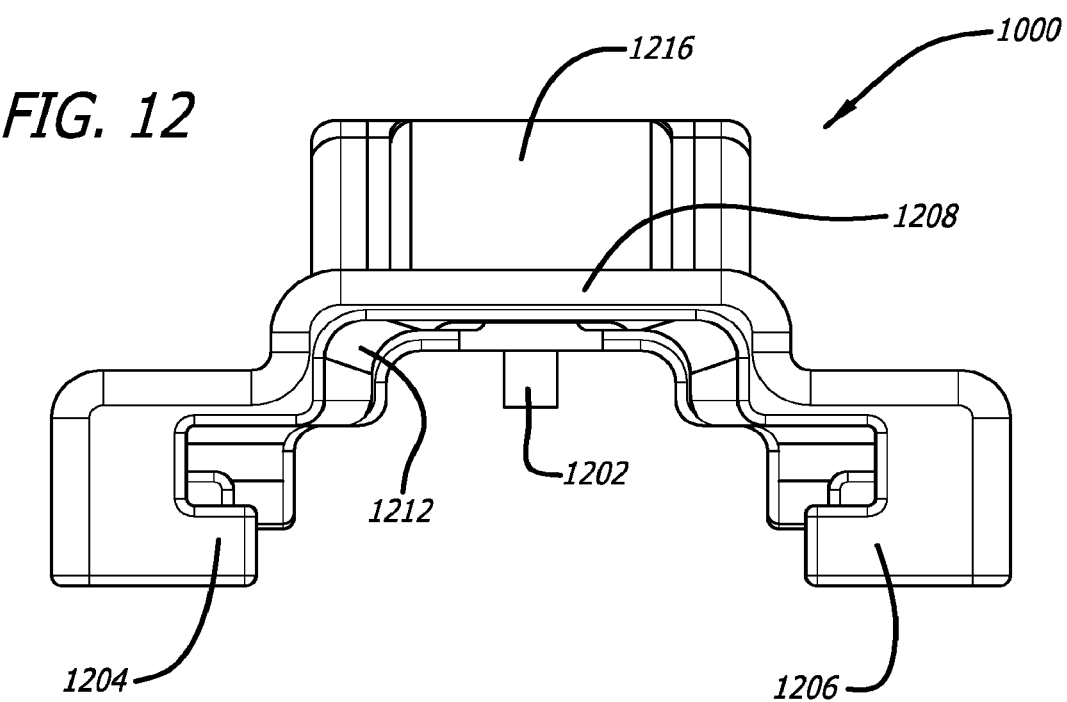
FIG. 12 illustrates a back view of the sensing and/or monitor device shown mounted onto a dry powder inhaler as shown in FIGS. 10 and 11.

FIGS. 10-16 depict alternate embodiments, wherein dry powder inhaler 900 includes detachable sensing and monitoring device 1000 presented as a jacket or cap, wherein detachable sensing and monitoring device 1000 can be provided as a detachable part that can adapt to a dry powder inhaler. In this embodiment, the jacket is manufactured as a separate, detachable device comprising sensors, for example, a microphone which can detect signals and being capable of storing, transmitting or displaying the signals. In one embodiment, the sensor is placed in the bottom portion of the jacket as depicted in FIG. 12 so that the sensor is placed in an air conduit of the inhaler. In other example embodiments, a wireless device can also be provided in connection with the sensor. Sound waves emanating from the inhaler in use with or without a dry powder are detected by the microphone and the signals can be analyzed and correlated to time of powder discharge in the presence of a dry powder, airflow rate, end of powder discharge during an inhalation maneuver, temperature within the inhaler pathway, and the like, depending on the type of sensor used. For example, an increase in sound can be correlated to an increase in flow rate through the device, and/or powder particles collisions in the air stream during delivery.

A sensor such as a microphone, as a result of its small size, can be placed anywhere in the inhaler. In embodiments wherein the sensor is a pressure transducer, the sensor can be placed within an air conduit passing through one of the inhaler compartments. The sensors can be provided, for example, in an air conduit on or within the inhaler or provided as a separate, detachable part as an accessory to the inhaler with a shape or configuration that can be adapted to the inhaler to which is to be adapted, and can include a cap, a jacket, sleeve or a saddle-like configuration that can be adapted or mounted to the inhaler. For the detachable embodiments, the sensing and monitoring apparatus is easy and inexpensive to manufacture and can be made from plastics, and works well with high resistance dry powder inhalers. In the embodiment illustrated in FIG. 10, for example, sensor 1202, depicted in FIG. 12, is provided within the air conduit of mouthpiece 904. The sensor can be any sensor, for example, a thermocouple wire, a pressure transducer, an analog sensor, a microphone, an optical sensor, a gas sensor, or any sensor that can detect signals generated within an inhaler. Sensor 1202, for example is a microphone. The sensors described herein can be adapted to communicate or transmit signals with a wireless device or the signals can be transmitted or stored using wire connection 916 to an analog to digital converter.

Alternatively, an analog to digital converter is provided within the inhaler device and resulting digital data is transferred out of the device directly. The signals provided by the sensors described herein can be in the form of sound generated in an inhaler by airflow passing through the air conduits and/or powder particles collisions entrained in the air flow pathway. Signals generated from the inhaler can be detected by the sensors and stored, transmitted or displayed. Data can be generated from the signals and qualitatively and/or quantitatively analyzed. In this manner, measurements can be made including time of dose release, FIG. 11 depicts an isometric view of the sensing and/or monitoring device illustrated in FIG. 10, wherein dry powder inhaler 900 is depicted in an open configuration. Dry powder inhaler 900 comprises mouthpiece 904, housing 906, and a hinge mechanism, including a gear, for opening and closing dry powder inhaler 900. Movement of mouthpiece 904 to an open configuration as shown in FIG. 11 permits mounting of cartridge 1102 for dosing. Movement of mouthpiece 904 onto housing 906 into a closed or dosing position, as illustrated in FIG. 9, of dry powder inhaler 900 which comprises a slide tray attached to the hinge mechanism, reconfigures cartridge 1102 to a dosing position forming an air pathway through cartridge 1102 and mouthpiece 904.

In one example embodiment, detachable sensing and monitoring device 1000 (FIGS. 12, 13, and 16) can be used as needed by a patient or a health provider in training or gathering information from the patient's inhalation maneuvers and then removed from dry powder inhaler 900, at which point dry powder inhaler 900 remains functional. FIG. 11 depicts an example embodiment wherein detachable sensing and monitoring device 1000 is adapted to mouthpiece 904 so that it fits securely and cannot move during loading or unloading cartridge 1102 with repeated use. Detachable sensing and monitoring device 1000 can be removed after use and remounted onto another inhaler as needed. In this embodiment, the detachable system provides a simple device that does not interfere with, or affect with the characteristic resistance values of the inhalation system.

FIG. 12 illustrates a back view of detachable sensing and monitoring device 1000 shown mounted onto dry powder inhaler 900 in FIGS. 10 and 11, removed from an inhaler. As illustrated in FIG. 12, detachable sensing and monitoring device 1000 is configured to have first flange 1204 and second flange 1206 both of which can engage mouthpiece 904 so that a secure fit can be obtained and can clear housing 906 by sitting within corresponding first groove 918 and second groove 920 on dry powder inhaler 900 when in a closed position. In such an example embodiment, dry powder inhaler 900 can comprise wire connection 916 or at least one lead which can couple to an analog to digital converter so that signals detected by sensor 1202 on traversing portion 1208 of detachable sensing and monitoring device 1000 can be transformed into data. In an alternate example embodiment, detachable sensing and monitoring device 1000 can be adapted to a wireless transmitter to send measured signals to a receiver.

Figure 13:
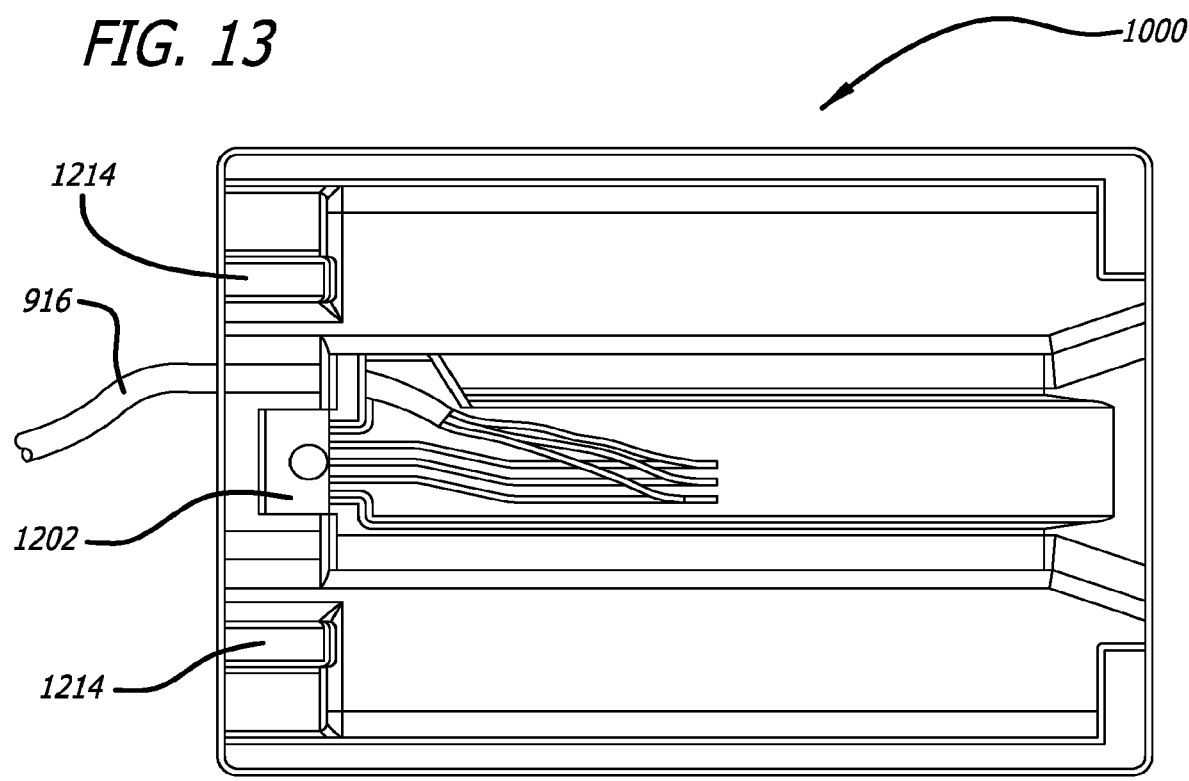
FIG. 13 illustrates a bottom view of the sensing and/or monitor device illustrated in FIG. 12.
Figure 16:
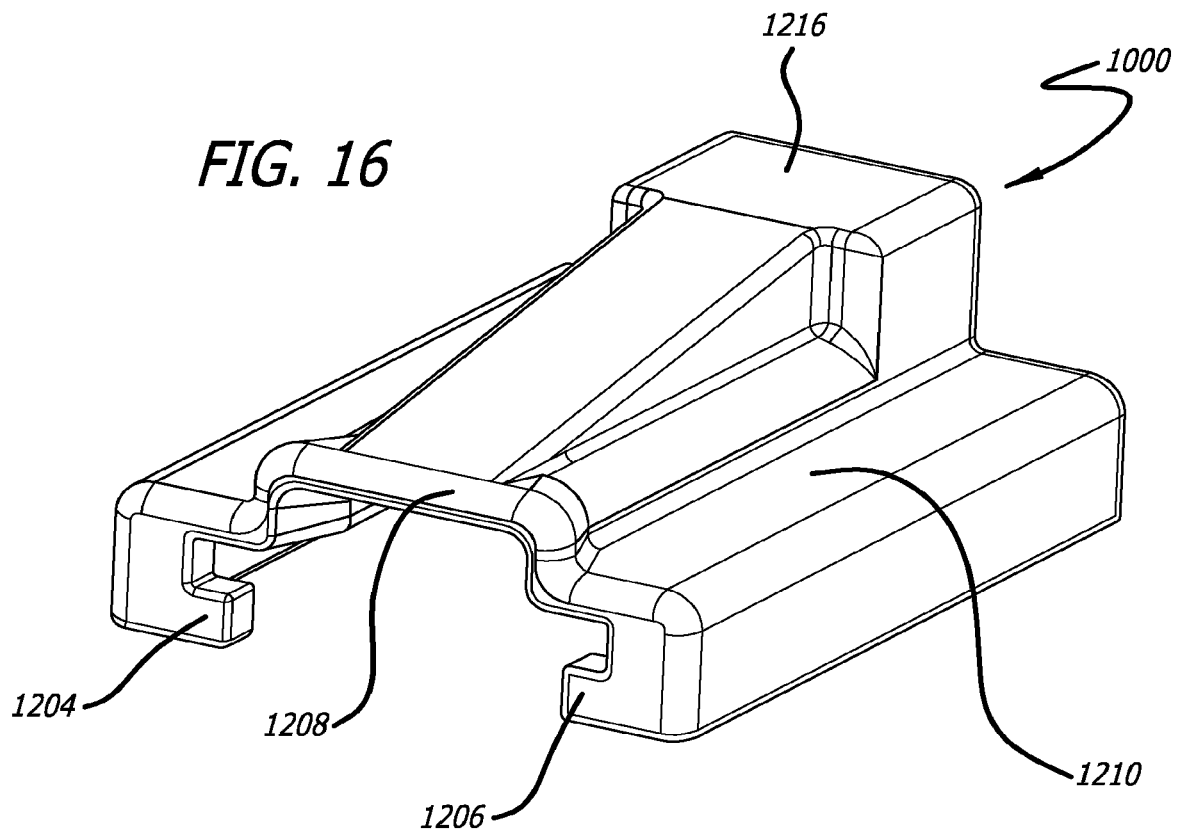
FIG. 16 illustrates an isometric view of the embodiment of the sensing and/or monitoring device depicted in FIGS. 10-15.

FIGS. 12 and 16 illustrate detachable sensing and monitoring device 1000 configured in the shape of a saddle to correspond to different dry powder inhaler configurations. Detachable sensing and monitoring device 1000 has top surface 1210, bottom surface 1212 and sensor 1202 configured on bottom surface 1212 of detachable sensing and monitoring device 1000 in a mid-longitudinal axis. Detachable sensing and monitoring device 1000 can also comprise at least one detent or at least one protrusion 1214 in addition to first flange 1204 and second flange 1206 to engage and adapt to dry powder inhaler 900. In one example embodiment, detachable sensing and monitoring device 1000 comprises a raised area 1216 with a hollow undersurface configured to hold sensor wires 1302 so as to avoid any obstruction of airflow in the air conduit of dry powder inhaler 900. FIG. 13 depicts a bottom view of detachable sensing and monitoring device 1000 illustrating sensor 1202 coupled to sensor wires 1302 and wire connection 916 for connecting to a digital to analogue converter.

FIG. 14 illustrates a cross-sectional side view of dry powder inhaler 900 equipped with detachable sensing and monitoring device 1000 shown in FIG. 11. The cross-section is through its mid-longitudinal line with cartridge 1102 in place and showing the position of sensor 1202 within the jacket. FIGS. 14 and 15 also show the position of sensor 1202, for example a microphone, in the air pathway of mouthpiece 904. In some embodiments, the sensor within the jacket for adapting to an inhaler's air pathways can be configured in different places depending on the inhaler. In this manner, the jacket can be configured to have the sensor integrated so when adapted to the inhaler it is position upstream, downstream or in the middle of the inhaler's air conduit so that the sound signals or vibrations can be detected through the wall of the inhaler or directly on the air pathway.

Figure 17:
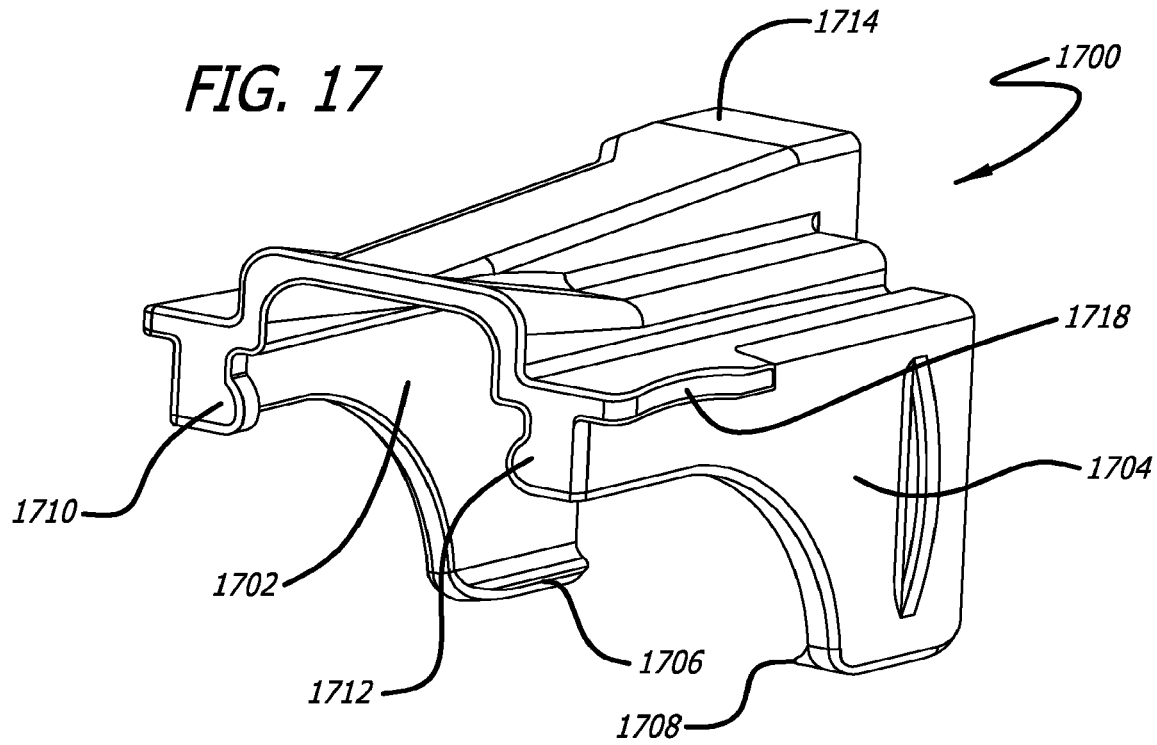
FIG. 17 illustrates an isometric view of an alternate embodiment of a sensing and/or monitoring device for adapting to a dry powder inhaler.

FIG. 17 depicts an isometric view of alternate detachable monitoring device 1700 configured to be adapted to a dry powder inhaler such as dry powder inhaler 900. In this example embodiment, first side panel 1702 and second side panel 1704 can adapt to first inhaler side panel 922 and second inhaler side panel 924 of mouthpiece 904 to form a tight fit with dry powder inhaler 900. Alternate detachable monitoring device 1700 further comprises first bottom flange 1706, second bottom flange 1708, first front flange 1710 and second front flange 1712 used to engage with dry powder inhaler 900. First bottom flange 1706 and second bottom flange 1708 grasp the bottoms of first inhaler side panel 922 and second inhaler side panel 924 while first front flange 1710 and second front flange 1712 grasp the sides of mouthpiece 904 and fit within first groove 918 and second groove 920 on dry powder inhaler 900. Alternate detachable monitoring device 1700 further includes raised area 1714 for housing a sensor and accompanying wires (not illustrated) in its undersurface. Grasping area 1718 facilitates handling of the jacket.

Figure 18:
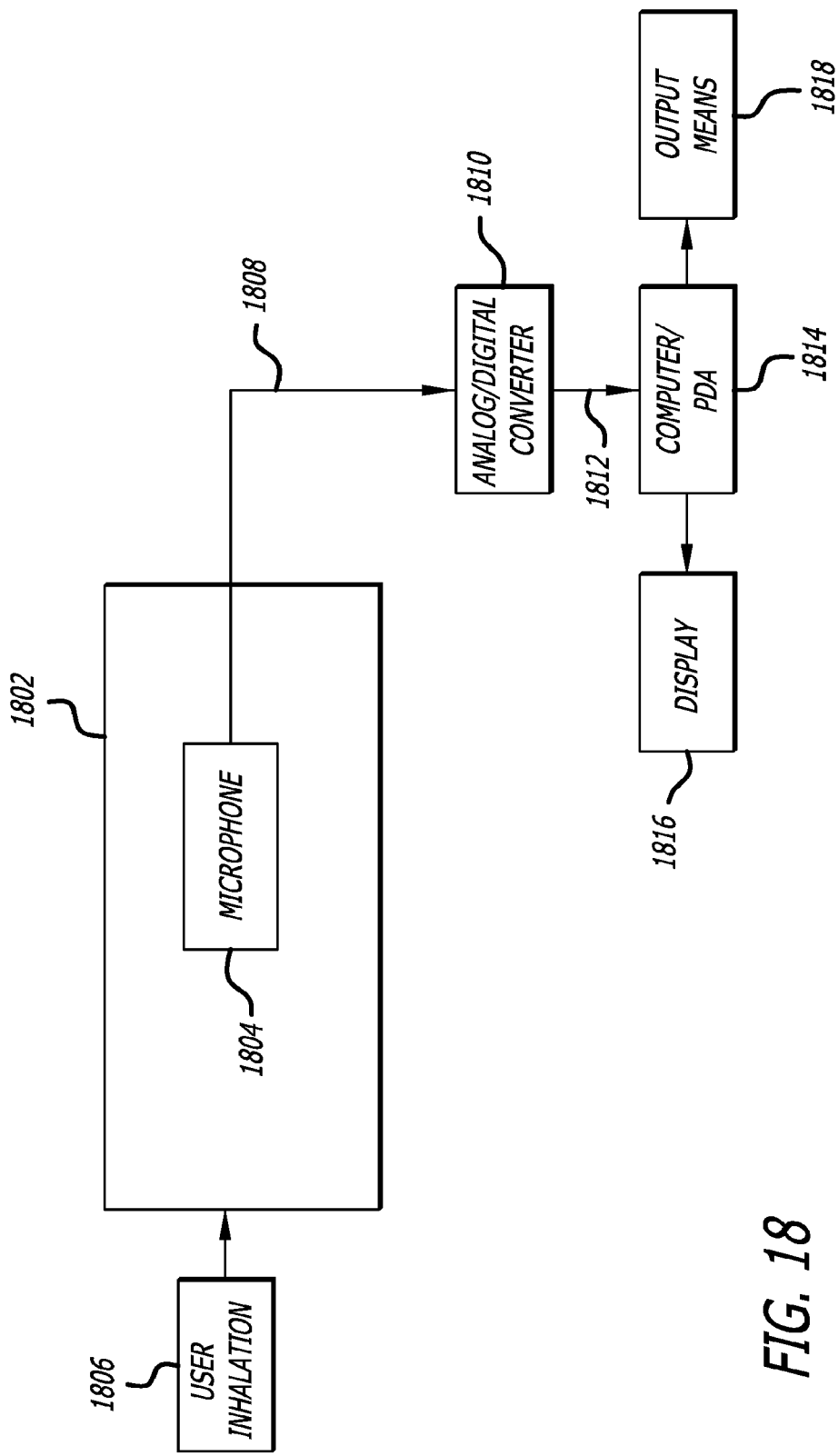
FIG. 18 illustrates a block diagram of the overall exemplary sensing and/or monitoring system disclosed herein.

FIG. 18 illustrates block diagram 1800 for an exemplary configuration of an overall sensing and/or monitoring device and system as disclosed herein. In such an example embodiment, inhaler 1802 comprises microphone 1804 to detect user inhalation 1806 and provide analog signal 1808. During user inhalation 1806, sound waves generated by the airflow as it enters the air conduits of inhaler 1802 are detected by microphone 1804. Microphone 1804 can detect sound signals generated from alteration in pressure, stress, particle displacement and particle velocity of an inhaler in use, the range from 15 to 20,000 Hertz. Microphone 1804 uses the signal pattern resulting from the changing or variations in frequency emissions intrinsically being generated from the inhaler in use with and without powder to determine the flow rate or pressure within the device that when analyzed can be correlated to user and/or device performance. These vibratory signals in microphone 1804 are then converted into analog signal 1808 (e.g. voltage) and transmitted to analog to digital converter 1810. Signals from the analog/digital converter 1812 are communicated to computer/PDA 1814 provided with a microprocessor which uses an algorithm for analyzing the signals received from the analog/digital converter 1812. The processed data is presented with frequency, time and amplitude parameters, and provided on display 1816 or provided to an output means 1818 for storage for future use, communication to a web based digital storage, and/or printing out. In such an example embodiment, by monitoring the signal frequency versus time, the amplitude of analog signal 1808 can be determined. Each dry powder inhaler type can have a typical acoustical pattern, or fingerprint, which develops for the inhaler in use, and the pattern can then be detected and converted to specific signals, analyzed and stored or displayed in a display device such as a computer monitor.

In one example embodiment, a sensing and monitoring system for an inhaler includes a sensing and/or monitoring device structurally configured to be adapted to an inhaler; an analog to digital converter; and a data storage medium. The data storage medium includes a disc drive, a CD-ROM, a server, a flash card or drive, memory card, and the like and includes a set of machine-readable instructions that are executable by a microprocessor or other processing device to implement an algorithm. The algorithm, when run, initiates the steps of generating a logical sub-system generation number derived from detected signals; saving the logical sub-system generation number to a data track within a logical sub-system, wherein the logical sub-system generation number and a cluster generation number in the processing device are compared; and storing and/or displaying information from the algorithm as the results from an inhalation maneuver.

Figure 19:
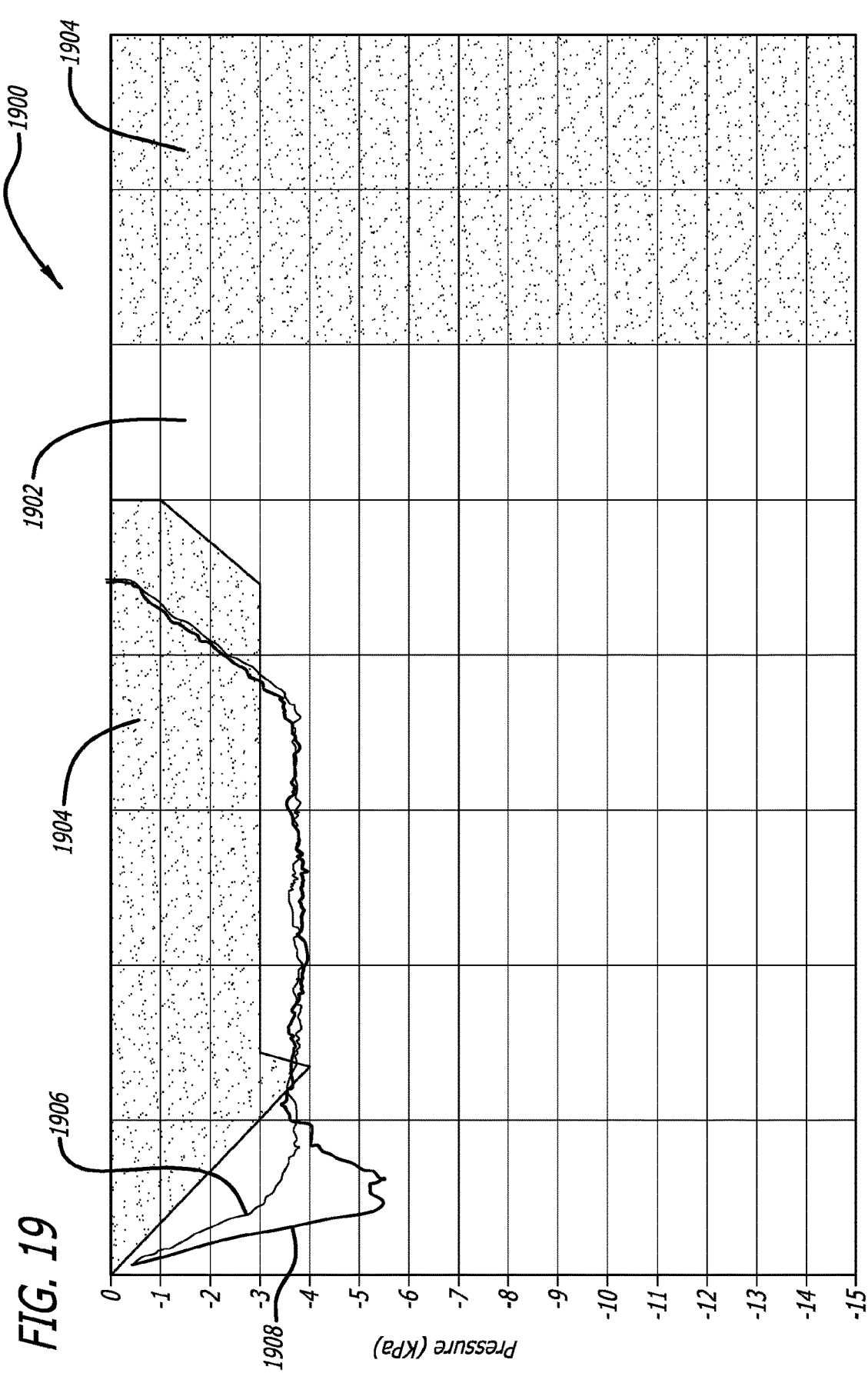
FIG. 19 graphically illustrates an inhalation maneuver performed by a subject trained to take a deep breath and illustrating profiles with and without a dry powder dose tested at the same pressure differential.

FIG. 19 illustrates an exemplary graphic display 1900 of an inhalation maneuver performed using a dry powder inhaler system in response to a pressure differential, wherein the dry powder inhaler system comprised a microphone sensor. Similar to FIGS. 6-9, graphic display 1900 has acceptable region 1902 and unacceptable region 1904. These regions can be colored red and green or any other combination of colors that aid in learning the inhalation maneuver. The subject is coached to take a deep breath with the inhaler for about a period of 4 to 5 seconds and allowed to exhale normally. The graph illustrates inspiratory profiles from the subject showing measurements using a sensing and monitor device described in FIGS. 10-16. FIG. 19 illustrates the data as time in the x-axis and pressure differential in the y-axis.

The inhalations maneuvers were performed using the inhaler with a cartridge without a dry powder formulation, depicted by first curve 1906, and with a dry powder formulation, depicted by second curve 1908. The results show that the sensing and monitoring device can detect the presence of powder emitted from the system, the time of powder emission and the amount of powder emitted from the system. Curve 1906 is the signal produced by the microphone during an inhalation without powder in the system and curve 1908 is the signal produced by the microphone during the same inhalation with powder in the system. The difference of the curves 1908 and 1906 represents the presence and magnitude of powder emitted from the system and time of emission. The data in FIG. 19 illustrate that the sensing and monitoring device is effective for measuring the amount of dose emitted from the inhaler cartridge system.

Example 1

Using an Integrated Training Device

A 57 year old Type II diabetic is instructed to receive inhaled insulin from a dry powder inhalation system, because she has an elevated hemoglobin A1c and is considered out of control. The patient is trained for inhalation using a device as illustrated in FIG. 9B with an integrated sensor. The patient is given the device and asked to take a deep rapid breath in using the training device.

The data is collected on a computer and the patient is able to view the data in real-time on a display screen. The patient's first inhalation attempt is too slow and is indicated on-screen as entering a red "unacceptable region." The patient is instructed to take another rapid breath in that is slightly faster than the previous attempt. Upon completion of the inhalation, the graph illustrates that the patient's inhalation maneuver was acceptable and entirely in the green region of the graph. Upon being comfortable with the training, the patient is clear for use of a similar device.

The patient is prescribed a dry powder inhaler similar to the type that illustrated in FIG. 9A and cartridges filled with an inhalable insulin for treatment of the patient's diabetes. Six months after prescribing the inhaled insulin, the patient's diabetes is diagnosed as under control.

Example 2

Using an Attachable Training Device

A 59 year old Type II diabetic is instructed to receive inhaled insulin from a dry powder inhalation system. The patient has requested the inhalation system for convenience reasons. The patient is trained for inhalation using a device as illustrated in FIG. 9A. The patient is given the device fitted with an attachable sensor similar to that if FIG. 12 and asked to take a deep rapid breath in using the training device.

The data is collected on a computer and the patient is able to view the data in real-time on a display screen. The patient's first attempt is acceptable as indicated by the software. Upon being comfortable with the training, the patient is clear for use of the device.

The patient attachable sensor is removed from the dry powder inhaler. The patient is given the dry powder inhaler and cartridges filled with inhalable insulin for treatment of the patient's diabetes. Six months after prescribing the inhaled insulin, the patient's diabetes is diagnosed as under control and the patient comments on the great convenience of the device.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for measuring pressure differential during an inhalation maneuver, comprising:
   providing a dry powder inhaler to a subject wherein said dry powder inhaler comprises an attachable monitoring system comprising:
   an interactive monitoring device comprising:
   at least one sensor configured to attach to, or within, a mouthpiece of said dry powder inhaler, wherein said at least one sensor is in communication with air conduits of said dry powder inhaler to measure real-time changes in air pressure or air flow and generate data;
   an analog to digital converter;
   a data storage medium, said data storage medium including a set of machine-readable instructions that are executable by a microprocessor to implement an algorithm, said algorithm comprising instructions for:
   manipulating said data;
   having said subject inhale for at least one second;
   transmitting and analyzing said data in real time generated from said subject;
   receiving said data from at least one sensor;
   filtering said data;
   transforming said data;
   analyzing said data; and
   monitoring the subject using said data in a display in real time.

2. The method of claim 1, wherein said at least one sensor is a pressure sensor, temperature sensor, sound sensor, or optical sensor.

3. The method of claim 1, wherein said inhalation maneuver causes said at least one sensor to generate data from said air conduits.

4. The method of claim 1, wherein said at least one sensor is a microphone.

5. The method of claim 1, wherein said interactive monitoring device is a detachable device.

6. The method of claim 1, wherein the at least one sensor detects at least one signal generated from said dry powder inhaler and transmits in real-time said at least one signal to at least one external device comprising a microprocessor by wireless communication for analysis of said at least one signal to generate a data set for real-time display of the inhalation maneuver concurrently being performed by said subject.

7. The method of claim 6, wherein said at least one signal is a sound signal.

8. The method of claim 6, wherein said at least one sensor is configured to further measure said at least one signal.

9. The method of claim 1, wherein said dry powder inhaler has a resistance value between about 0.065 ($\sqrt{kPa}$)/liter per minute and about 0.200 ($\sqrt{kPa}$)/liter per minute.

10. A method for monitoring an inhalation maneuver in real-time corresponding to characteristic patterns of a patient's use of a dry powder inhalation system, comprising:
    providing a dry powder inhaler to the patient, said dry powder inhaler includes
    a mouthpiece,
    a unit dose cartridge structurally configured for said dry powder inhaler, and
    an attachable interactive training device comprising
    at least one sensor attached to or within the mouthpiece in communication with inhaler air conduits of said dry powder inhaler, wherein the at least one sensor detects at least one signal generated from said dry powder inhaler and transmits in real-time by wireless communication said at least one signal to at least one external device comprising a microprocessor for analysis of said at least one signal to generate data for real-time display of an inhalation maneuver concurrently being performed by the patient.

11. The method for monitoring an inhalation maneuver of claim 10, wherein said at least one signal is derived from a pressure differential generated in said dry powder inhaler.

12. The method for monitoring an inhalation maneuver of claim 10, wherein the at least one signal is a sound signal.

13. The method for monitoring an inhalation maneuver of claim 10, wherein said at least one sensor is a pressure sensor, temperature sensor, sound sensor, or optical sensor.

14. The method for monitoring an inhalation maneuver of claim 10, wherein said unit dose cartridge comprises a dry powder for pulmonary delivery.

15. The method for monitoring an inhalation maneuver of claim 10, wherein the dry powder comprises diketopiperazine microparticles.

16. The method for monitoring an inhalation maneuver of claim 10, wherein the dry powder comprises at least one active ingredient.

17. The method for monitoring an inhalation maneuver of claim 10, wherein said dry powder inhaler has a resistance value between about 0.065 ($\sqrt{kPa}$)/liter per minute and about 0.200 ($\sqrt{kPa}$)/liter per minute.

18. The method for monitoring an inhalation maneuver of claim 13, wherein an analog to digital converter communicates said at least one sound signal from the sound sensor to a microprocessor configured to analyze and process said at least one sound signal for said characteristic pattern.

19. The method for monitoring an inhalation maneuver of claim 10, wherein said at least one external device comprises an analog to digital converter.

20. The method for monitoring an inhalation maneuver of claim 10, wherein said at least one external device comprises a display device.

* * * * *